(12) United States Patent
Wesner et al.

(10) Patent No.: US 10,434,485 B2
(45) Date of Patent: *Oct. 8, 2019

(54) COMPOSITIONS COMPRISING ENCAPSULATED ACTIVES WITHIN DROPLETS AND OTHER COMPARTMENTS

(71) Applicants: The Procter & Gamble Company, Cincinnati, OH (US); President and Fellows of Harvard College, Cambridge, MA (US)

(72) Inventors: John Christopher Wesner, Liberty Township, OH (US); Marco Caggioni, Cincinnati, OH (US); Taotao Zhu, West Chester, OH (US); David A Weitz, Bolton, MA (US); Alireza Abbaspourrad, Ithaca, NY (US); Chang-Hyung Choi, Belmont, MA (US)

(73) Assignees: The Procter & Gamble Company, Cincinnati, OH (US); President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/635,340

(22) Filed: Jun. 28, 2017

(65) Prior Publication Data
US 2017/0296996 A1 Oct. 19, 2017

Related U.S. Application Data

(63) Continuation of application No. 14/945,475, filed on Nov. 19, 2015, now Pat. No. 9,718,044.

(60) Provisional application No. 62/083,729, filed on Nov. 24, 2014.

(51) Int. Cl.
| | | |
|---|---|---|
| *B01J 13/06* | (2006.01) | |
| *C09K 15/08* | (2006.01) | |
| *C11B 9/00* | (2006.01) | |
| *A61Q 13/00* | (2006.01) | |
| *A61K 8/11* | (2006.01) | |
| *B01F 5/04* | (2006.01) | |
| *A61K 9/50* | (2006.01) | |
| *B01F 13/00* | (2006.01) | |
| *B01F 3/08* | (2006.01) | |
| *A61K 8/81* | (2006.01) | |
| *A61K 8/86* | (2006.01) | |
| *B01F 5/02* | (2006.01) | |
| *B01J 13/14* | (2006.01) | |
| *B01F 5/00* | (2006.01) | |

(52) U.S. Cl.
CPC ............ *B01J 13/06* (2013.01); *A61K 8/11* (2013.01); *A61K 8/8129* (2013.01); *A61K 8/86* (2013.01); *A61K 9/5089* (2013.01); *A61Q 13/00* (2013.01); *B01F 3/0807* (2013.01); *B01F 5/02* (2013.01); *B01F 5/045* (2013.01); *B01F 13/0062* (2013.01); *B01J 13/14* (2013.01); *C09K 15/08* (2013.01); *C11B 9/0046* (2013.01); *A61K 2800/412* (2013.01); *A61K 2800/56* (2013.01); *B01F 2003/0834* (2013.01); *B01F 2003/0838* (2013.01); *B01F 2005/0034* (2013.01); *Y10T 428/2984* (2015.01)

(58) Field of Classification Search
None
See application file for complete search history.

(56) References Cited

U.S. PATENT DOCUMENTS

| | | | |
|---|---|---|---|
| 6,221,332 B1 | 4/2001 | Thumm et al. | |
| 8,367,004 B2 | 2/2013 | Panagiotou et al. | |
| 9,718,044 B2 * | 8/2017 | Wesner | C09K 15/08 |
| 2002/0034550 A1 * | 3/2002 | Quong | A01N 25/28 |
| | | | 424/489 |

(Continued)

FOREIGN PATENT DOCUMENTS

| | | |
|---|---|---|
| WO | WO 2007003599 A2 | 1/2007 |
| WO | WO 201021307 | 10/2010 |

OTHER PUBLICATIONS

Takahiro Kawakatsu, et al., "Production of W/O/W emulsions and S/O/W pectin mmicrorcapsules by microchannel emulsification", Colloids and Surfaces A: Physiochemical and Engineering Aspects 189 (2001), pp. 257-264.

(Continued)

Primary Examiner — Marc S Zimmer
(74) Attorney, Agent, or Firm — James E Oehlenschlager

(57) ABSTRACT

The present invention generally relates to microparticles and, in particular, to systems and methods for encapsulation within microparticles. In one aspect, the present invention is generally directed to microparticles containing entities therein, where the entities contain an agent that can be released from the microparticles, e.g., via diffusion. In some cases, the agent may be released from the microparticles without disruption of the microparticles. The entities may be, for instance, polymeric particles, hydrogel particles, droplets of fluid, etc. The entities may be contained within a fluid that is, in turn, encapsulated within the microparticle. The agent may be released from the entity into the fluid, and then from the fluid through the microparticle. In such fashion, the release of agent from the microparticle may be controlled, e.g., over relatively long time scales. Other embodiments of the present invention are generally directed to methods of making such microparticles, methods of using such microparticles, microfluidic devices for making such microparticles, and the like.

1 Claim, 5 Drawing Sheets

(56) References Cited

U.S. PATENT DOCUMENTS

| | | |
|---|---|---|
| 2009/0012187 A1 | 1/2009 | Chu et al. |
| 2009/0131543 A1 | 5/2009 | Weitz et al. |
| 2009/0155586 A1 | 6/2009 | Maitra et al. |
| 2011/0230390 A1 | 9/2011 | Ouali et al. |
| 2013/0316007 A1 | 11/2013 | Xiaojun et al. |
| 2014/0220350 A1 | 8/2014 | Kim et al. |

OTHER PUBLICATIONS

Isao Kobayashi et al., "Preparation of Monodisperse Water-in-Oil-in-Water Emulsions Using Microfluidization and Straight-Through Microchannel Emulsification", Journal article AOCS Press, vol. 82, No. 1, Jan. 13, 2005, pp. 65-71.

Nauman Khalid et al., "Monodisperse W/O/W emulsions encapsulating L-ascorbic acid: Insights on their formulation using microchannel emulsification and stability studies", Colloids and Surfaces A: Physiochemical and Engineerings Aspects 458 (2014) pp. 69-77.

International Search Report and Written Opinion dated Feb. 10, 2016, 12 pgs.

International Search Report and Written Opinion dated Feb. 11, 2016, 12 pgs.

Bing Jie Sun et al. "Microfluidic Melt Emulsification for Encapsulation and Release of Actives", ACS Applied Materials and Interfaces, American Chemical Society, US, vol. 2, No. 12, Dec. 22, 2010, pp. 3411-3416, XP008145173, ISSN: 1944-8244.

Wynter J Duncanson et al. "Microfluidic Synthesis of Advanced Microparticles for Encapsulation and Controlled Release", Lab on a Chip, vol. 12, No. 12, Jan. 1, 2012, p. 2135, XP055185215, ISSN:1473-0197.

Shin-Hyun Kim et al. "Polymersomes Containing a Hydrogel Network for High Stability and Controlled Release", SMALL, vol. 9, No. 1, Sep. 7, 2012, pp. 124-131, XP055248532, DE ISSN: 1613-6810.

David Baah et al. "Microfluidics for Particle Synthesis from Photocrosslinkable Materials", Microfluidics and Nanofluidics, vol. 17, No. 3, Jan. 19, 2014, pp. 431-455, XP055248949, DE ISSN: 1613-4982.

\* cited by examiner

COMPOSITIONS COMPRISING ENCAPSULATED ACTIVES WITHIN DROPLETS AND OTHER COMPARTMENTS

FIELD

The present invention generally relates to microparticles and, in particular, to systems and methods for encapsulation within microparticles.

BACKGROUND

Microparticles such as microcapsules have great potential for applications involving encapsulation, delivery, and release of agents in fields such as agriculture, health care, cosmetics and detergents, construction chemicals, and food and beverages. A variety of physical and chemical methods, including spray-drying, coextrusion, interfacial polymerization, and complex coacervation, have been used for high-throughput preparation of microparticles. For example, using various microfluidic technologies, a variety of agents have been encapsulated into emulsions, which are then solidified to form solid microparticles or other types of particles, for instance, by interfacial polycondensation, freezing, or polymerization. However, improvements in particle technologies are still needed.

In formulated products containing high levels of surfactants as well as microparticles with oil based payloads, the presence of the surfactants tends to increase the likelihood of the migration of the payload out of the micro particles and decrease the useful shelf life of the product. Microparticles having greater payload stability when disposed in an environment having a high concentration of surfactants are desired.

SUMMARY

The present invention generally relates to microparticles and, in particular, to systems and methods for encapsulation within microparticles. The subject matter of the present invention involves, in some cases, interrelated products, alternative solutions to a particular problem, and/or a plurality of different uses of one or more systems and/or articles.

In one aspect, the present invention is generally directed to a method. In some cases, the method is a method of release of agent from a particle, such as a microparticle. In one set of embodiments, the method includes an act of exposing, to an environment, a plurality of microparticles comprising a shell and a fluid within the shell, the fluid comprising a plurality of entities containing an agent, and causing release of at least about 50 wt % of the agent from the plurality of microcapsules without disruption of the shell.

The present invention, in another aspect, is generally directed to a composition. In one set of embodiments, the composition comprises a plurality of microparticles comprising a shell and a fluid within the shell, the fluid comprising a plurality of entities containing an agent, where at least 50 wt % of the agent is releasable from the microparticles without disruption of the shell. According to another set of embodiments, the composition comprises a plurality of microparticles comprising a shell and a fluid within the shell, the fluid comprising a plurality of entities containing an agent, where the plurality of entities within the shell has a volume of at least 50% of the volume of the shell.

In one aspect, a composition includes a plurality of microparticles. Each microparticle includes a single core which contains a liquid emulsion having a dispersed phase and a continuous phase; and a shell surrounding the single core. The shell has a mean wall thickness of between about 0.1 µm, and about 10 µm.

In one aspect, a composition includes a plurality of microparticles. Each microparticle includes a single core which contains a liquid emulsion having a dispersed phase and a continuous phase; and a shell surrounding the single core. The shell has a mean wall thickness of between about 0.1 µm, and about 10 µm. The core comprises an aqueous phase, an oil phase, and a surfactant.

In another aspect, the present invention encompasses methods of making one or more of the embodiments described herein, for example, microfluidic droplets encapsulating entities.

In one aspect, the method is directed to the production of microparticles and includes the steps of: providing a first liquid to a system of microfluidic devices, introducing a stream of the first liquid into a stream of a second liquid, introducing a stream of a third liquid which surrounds the second liquid, and forming droplets within the third liquid. The first liquid includes an emulsion having a dispersed phase and a continuous phase as it is introduced into the second liquid. The continuous phase of the first liquid is substantially immiscible in the second liquid. The droplets comprise a core including the first liquid and a shell comprised of the second liquid.

In one aspect, an apparatus for producing microparticles includes: a first reservoir containing a first liquid, a second reservoir containing a second liquid, and a third reservoir containing a third liquid. The first liquid includes an emulsion. The emulsion includes a dispersed phase and a continuous phase. The continuous phase of the emulsion is substantially immiscible in the second fluid. The first reservoir is in fluid communication with the first conduits of a plurality of microfluidic devices. The first conduitshave exits. The second reservoir in is fluid communication with second conduits. The second conduits at least partially surround the first conduits. The third reservoir is in fluid communication with the second conduits. The apparatus also includes third conduits disposed, at least in part, within the second conduits, downstream of the exits of the first conduits.

In still another aspect, the present invention encompasses methods of using one or more of the embodiments described herein, for example, microfluidic droplets encapsulating entities.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to microparticles and, in particular, to systems and methods for encapsulation within microparticles. In one aspect, the present invention is generally directed to microparticles containing entities therein, where the entities contain an agent that can be released from the microparticles, e.g., via diffusion. In some cases, the agent may be released from the microparticles without disruption of the microparticles. The entities may be, for instance, polymeric particles, hydrogel particles, droplets of fluid, etc. The entities may be contained within a fluid that is, in turn, encapsulated within the microparticle. The agent may be released from the entity into the fluid, and then from the fluid through the microparticle. In such fashion, the release of agent from the microparticle may be controlled, e.g., over relatively long time scales. Other embodiments of the present invention are generally directed to methods of making such microparticles, methods of using such microparticles, microfluidic devices for making such microparticles, and the like.

Figure 3:
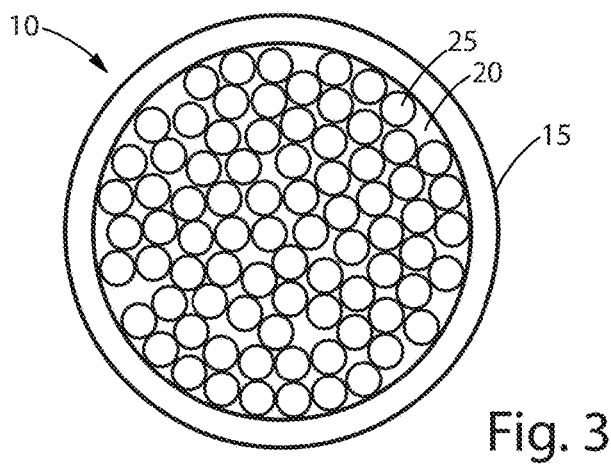
FIG. 3 illustrates the structure of a microparticle, in yet another embodiment of the invention.

One aspect of the invention is now described with reference to FIG. 3. In this example figure, a microparticle 10 comprises a shell 15 surrounding a fluid 20. Within fluid 20 are a plurality of entities 25. The entities may be, for example, polymeric particles, hydrogel particles, droplets of an immiscible fluid, or the like. The entities may also contain an agent 30 to be released from microparticle 10. To be released, agent 30 must travel from entities 25 through fluid 20 and shell 15. In some cases, shell 15 may be kept intact or undamaged during the release of agent 30. Thus, agent 30 may diffuse out of entities 25, through fluid 20, and through shell 15, before being released from microparticle 10. Accordingly, the microparticles, in certain embodiments, can provide for the controlled rate of release of agent 30.

In one embodiment, the fluid 20 comprises an emulsion comprising a continuous phase and a dispersed phase. The entities may comprise the dispersed phase of the emulsion. In such embodiments, the continuous phase may constitute an aqueous phase and the dispersed phase may constitute an oil phase. The fluid may further comprise a surfactant. In one embodiment, the first fluid may comprise a suspo-emulsion comprising a continuous phase and particles suspended in the continuous phase.

Exemplary emulsions may be created by dispersing an oil phase material in an aqueous phase with mechanical agitation. Exemplary forms of mechanical agitation include: shaking, mixing, agitators, sonication, colloid mills, rotors, rotor-stator, static mixers, flow-through static mixers, homogenizers, high-shear microfluidic collision processors, a Microfluidizer®, vortex mixers, a speed mixer, and a high shear homogenizer. Exemplary emulsions include an emulsion of 0.1-0.4 wt % Permulen TR-2 surfactant in perfume oil, and an emulsion of α-pinene in a solution of 2.5% (v/v) PVA and 2% (w/w) Tween 80.

Exemplary continuous phase materials for the first liquid include: water, glycerine, formamide, dimethyl formamide, dimethyl sulfoxide, polyethylene glycol, propylene glycol, and fluorinated oils.

In some cases, the release profile may be relatively slow, e.g., having a characteristic time of release of hours or days. In addition, in certain embodiments, the rate of release of agent from the microparticle may not necessarily be controlled by the amount of agent contained within the microparticle; for example, diffusion of the agent through the fluid may be rate-limiting, and the entities may act as a reservoir to contain agent prior to diffusion through the fluid. In contrast, in other particles loaded with agent, the amount and rate of agent released from the particle is usually a function of the amount of agent contained within the particle.

In some cases, the microparticles may be exposed to an environment to which the agent is to be released. The agent may be caused to be released from the microparticles via a variety of techniques. The release of agent may occur without disrupting the microparticles, e.g., by damaging the shell of the microparticles to release the agent from within. In one set of embodiments, the agent may be released by agitating the microparticles. In another set of embodiments, the microparticles may be exposed to a fluid, such as oil (e.g., a hydrocarbon oil, crude oil, petroleum, etc.), or to water. In some cases, the agent may diffuse through the microparticles to be released at the surface of the microparticles into the surrounding environment, e.g., if the microparticles are contained in a fluid, such as an oil or water.

Figure 4:
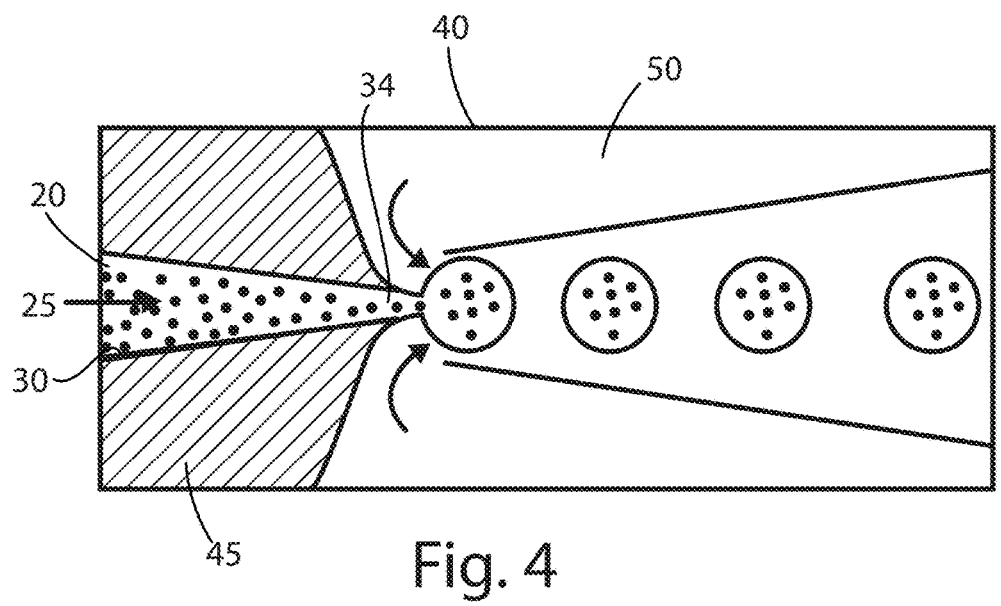
FIG. 4 illustrates a device for producing particle suspensions, in still another embodiment of the invention.

The microparticles may be produced by a variety of techniques. For example, FIG. 4 describes one non-limiting system for producing such microparticles. In this figure, a fluid 20 containing entities 25 suspended therein flows through a first channel 30. As discussed below, fluid 20 becomes encapsulated within microparticles. In addition, first channel 30 has an exit opening 34 contained within channel 40. Also contained in channel 40 is fluid 45, which will be used to produce the shell of the microparticle, and fluid 50, which will contain the microparticles. In this figure, fluid 45 flows around channel 30 towards exit opening 34 of channel 30, where it surrounds fluid 20 emerging out of the exit opening. In turn fluid 45 is surrounded by fluid 50. Fluids 45 and 50 may be substantially immiscible in certain embodiments. At exit opening 34, multiple emulsion droplets may be formed, containing fluid 20, surrounded by droplets of fluid 45, contained within continuous fluid 50. Fluid 45 may also be hardened or reacted to form a shell surrounding fluid 20 by, for example, exposing the formed droplet to appropriate electromagnetic radiation. See also Int. Pat. Apl. Pub. Nos. WO 2006/096571 or WO 2013/006661, each incorporated herein by reference in its entirety, for other examples.

The above discussion illustrates non-limiting examples of certain embodiments of the present invention generally directed to fluids encapsulated within microparticles. However, other embodiments are also possible. Accordingly, more generally, various aspects of the invention are directed to various systems and methods for encapsulation within microparticles For instance, in one aspect, the microparticles may comprise a plurality of entities therein containing one or more agents. Any suitable entities able to contain an agent and remain as separate entities when contained within a fluid may be used. The entities may be solid, or fluid in some embodiments.

In one set of embodiments, for example, the entities may be a second fluid that is substantially immiscible within the fluid within the microparticles. However, the entities may be substantially prevented from merging or coalescing together using surfactant or other suitable techniques. Thus, the entities are able to remain as discrete or separate entities within the fluid. Thus, for example, if the fluid within the microparticles is aqueous (e.g., a "water" phase), the fluid forming the entities may be a non-aqueous fluid that is substantially immiscible within the aqueous fluid (e.g., an "oil" phase), or vice versa.

In one embodiment, the entities may comprise a fluid which is substantially miscible in the shell of the microparticles.

It should be understood that the "water" phase is not limited to only pure water, but may be any fluid miscible in water, and/or the fluid may be water but contain other substances dissolved or suspended therein, etc. Similarly, the "oil" phase need not be a hydrocarbon oil, but may be any fluid that is substantially immiscible in water. Accordingly, the terms "oil" and "water" are used as terms of convenience, as is typically expressed by those of ordinary skill in the art.

The entities contained within the microparticles need not be fluid. In another set of embodiments, the entities may be particles, for example, polymeric particles or hydrogel particles, etc. Any of a wide variety of particles may be used, for example, that can be contained or suspended in a fluid that is to be encapsulated within a microparticle. For example, the entities may comprise hydrogels such as agarose, polyacrylamide, poly(N-isopropylacrylamide), or the like, or polymers such as polystyrene, polypropylene, polyethylene, polycaprolactone, polyisoprene, poly(lactic acid), polycaprolactone, poly(lactic acid), polyacrylonitrile, polyimide, polyamide, and/or mixtures and/or co-polymers of these and/or other polymers. The polymeric particles may be formed using microfluidic techniques known to those of ordinary skill in the art, or using other techniques that are not necessarily microfluidic. In some cases, the particles are nanoparticles e.g., having an average diameter of less than 1 micrometer.

Any suitable number of entities may be contained within a microparticle. In some embodiments, however, there may be a relatively large number of entities contained within a microparticle, e.g., if the entities are relatively small relative to the size of the microparticles. In some cases, entities with relatively high loading densities may be achieved, as discussed herein, by starting with a fluid having a relatively high loading density of such entities.

The entities may be relatively small in some embodiments. For example, the entities may have an average diameter of less than about 1 micrometer, less than about 500 nm, less than about 300 nm, less than about 200 nm, less than about 100 nm, less than about 50 nm, less than about 30 nm, less than about 20 nm, or less than about 10 nm, etc. The entity may be spherical or non-spherical. The average diameter of a non-spherical entity may be taken as the diameter of a perfect sphere having the same volume as the non-spherical entity.

In another set of embodiments, the entities may have an average diameter that is less than about 30%, less than about 20%, less than about 15%, less than about 10%, less than about 5%, less than about 3%, less than about 2%, less than about 1%, less than about 0.5%, less than about 0.3%, less than about 0.2%, less than about 0.1%, or less than about 0.05% of the average diameter of the microparticle containing the entities. The diameter or volume of the entities may be determined directly, e.g., using optical or electron microscopy, and or estimated, e.g., based on the overall volume of entities contained within the microparticles.

In one set of embodiments, the microparticles may each contain, on average, at least about 100, at least about 200, at least about 300, at least about 500, at least about 1000, at least about 2000, at least about 3000, at least about 5000, at least about 10,000, at least about 20,000, at least about 300,000, or at least about 500,000 entities therein. The microparticles may also, in some cases, exhibit a relatively uniform distribution of entities per microparticles.

In some cases, the entities may exhibit a core loading within microparticle such that the entities take up at least about 1%, at least about 50%, at least about 60%, at least about 70%, at least about 75%, at least about 80% at least about 85%, at least about 90%, at least about 95%, at least about 97%, at least about 98%, at least about 99%, at least about 99.5%, or at least about 99.7% of the volume of the interior of the microparticle (i.e., not including the volume of the shell). Such relatively high loadings of entities are surprising and not routinely achievable in many microfluidic prior art techniques. In one embodiment, the core of the microparticle comprises about 20% continuous phase and about 80% dispersed phase.

In one embodiment, the core loading of the dispersed phase may be between about 1% and about 80% of the volume of the interior of the particle. In one embodiment, the core loading of the dispersed phase may be between about 50% and about 70% of the volume of the interior of the particle.

The entities may, in some cases, be relatively monodisperse. For example, the entities within a microparticle may have an overall average diameter and a distribution of diameters such that no more than about 5%, no more than about 2%, or no more than about 1% of the particles or droplets have a diameter less than about 90% (or less than about 95%, or less than about 99%) and/or greater than about 110% (or greater than about 105%, or greater than about 101%) of the overall average diameter of the plurality of entities. However, in other cases, the entities may not necessarily be relatively monodisperse.

The entities may contain one or more than one agent, in any suitable distribution. For example, a microparticle may contain a first entity containing a first agent and a second entity containing a second agent, or an entity containing both first and second agents, or the like. If more than one microparticle is present, the microparticles may independently contain the same or different agents, at the same or different concentrations, etc.

Any suitable concentration of agent may be present within the entities. For instance, the agent may be present within the entities at a concentration of at least about 0.001 M, at least about 0.003 M, at least about 0.005 M, at least about 0.01 M, at least about 0.03 M, at least about 0.05 M, at least about 0.1 M, at least about 0.3 M, at least about 0.5 M, at least about 1 M, etc. The type or concentration of agent used may depend, for example, on the particular application.

Thus, the systems and methods described herein can be used in a plurality of applications. For example, fields in which the microparticles described herein may be useful include, but are not limited to, food, beverage, health and beauty aids, paints and coatings, chemical separations, agricultural applications, and drugs and drug delivery. For instance, a precise quantity of a fluid, drug, pharmaceutical, or other agent can be contained in an entity. Non-limiting examples include biochemical species such as nucleic acids such as siRNA, RNAi and DNA, proteins, peptides, or enzymes. Additional agents that may be used include, but are not limited to, colloidal particles, magnetic particles, nanoparticles, quantum dots, fragrances, perfumes, proteins, indicators, dyes, fluorescent species, chemicals, biocides, or the like. Exemplary perfume materials may comprise a material selected from the group consisting of prop-2-enyl 3-cyclohexylpropanoate, (4aR,5R,7aS,9R)-octahydro-2,2,5, 8,8,9a-hexamethyl-4h-4a,9-methanoazuleno(5,6-d)-1,3-dioxole, (3aR,5aS,9aS,9bR)-3a,6,6,9a-tetramethyl-2,4,5,5a,7, 8,9,9b-octahydro-1H-benzo[e][1]benzofuran, 4-methoxybenzaldehyde, benzyl 2-hydroxybenzoate, 2-methoxynaphthalene, 3-(4-tert-butylphenyl)propanal, 3a,6,6,9a-tetramethyl-2,4,5,5a,7,8,9,9b-octahydro-1H-benzo[e][1]benzofuran, 3,7-dimethyloct-6-en-1-ol, 3,7-dimethyloct-6-enenitrile, 3-(4-tert-butylphenyl)butanal, 3-(4-propan-2-ylphenyl)butanal, (E)-1-(2,6,6-trimethyl-1-cyclohexa-1,3-dienyl)but-2-en-1-one, decanal, (E)-1-(2,6,6-trimethyl-1-cyclohex-3-enyl)but-2-en-1-one, (5E)-3-methylcyclopentadec-5-en-1-one, 2,6-dimethyloct-7-en-2-ol, ethyl 2-methylpentanoate, ethyl 2-methylbutanoate, 1,3, 3-trimethyl-2-oxabicyclo[2,2,2]octane, 2-methoxy-4-prop-2-enylphenol, 3a,4,5,6,7,7a-hexahydro-4,7-methano-1H-indenyl acetate, 3-(3-propan-2-ylphenyl)butanal, a,4,5,6,7, 7a-hexahydro-1H-4,7-methanoinden-1-yl propanoate, (2E)-3,7-dimethylocta-2,6-dien-1-ol, (12E)-1-oxacyclohexadec-12-en-2-one, [2-[1-(3,3-dimethylcyclohexyl)ethoxy]-2-methylpropyl]propanoate, hexyl acetate, 2-(phenylmethylidene)octanal, hexyl 2-hydroxybenzoate, (E)-4-(2,6,6-trimethyl-1-cyclohex-2-enyl)but-3-en-2-one, (E)-4-(2,6,6-trimethyl-1-cyclohexenyl)but-3-en-2-one, (E)-3-methyl-4-(2,6,6-trimethyl-1-cyclohex-2-enyl)but-3-en-2-one, 1-(2,3,8,8-tetramethyl-1,3,4,5,6,7-hexahydronaphthalen-2-yl)ethanone, propan-2-yl 2-methylbutanoate, (1R,2S, 5R)-5-methyl-2-propan-2-ylcyclohexan-1-ol, (E)-2-ethyl-4-(2,2,3-trimethyl-1-cyclopent-3-enyl)but-2-en-1-ol, 2,4-dimethylcyclohex-3-ene-1-carbaldehyde, 3,7-dimethylocta-1,6-dien-3-ol, 3,7-dimethylocta-1,6-dien-3-yl acetate, 1-((3R,3aS,7R,8aS)-2,3,4,7,8,8a-hexahydro-3,6,8,8-tetramethyl-1H-3a,7-methanoazulen-5-yl)-ethanone, methyl 3-oxo-2-pentylcyclopentaneacetate, 2-methylundecanal, 2-[2-(4-methyl-1-cyclohex-3-enyl)propyl]cyclopentan-1-one, 1-(5,5-dimethyl-1-cyclohexenyl)pent-4-en-1-one, 2-cyclohexylidene-2-phenylacetonitrile, 2-phenylethanol, 3,7-dimethyloctan-3-ol, 5-heptyloxolan-2-one, (2-tert-butylcyclohexyl)acetate, (E)-4-methyldec-3-en-5-ol, (4-tert-butylcyclohexyl)acetate, decahydro-2,2,6,6,7,8,8-heptamethyl-2H-indeno(4,5-b)furan, 17-oxacycloheptadec-6-en-1-one, pentyl 2-hydroxybenzoate, benzyl acetate, 4-phenylbutan-2-one, 2-methoxynaphthalene, 1,7,7-trimethylbicyclo[2.2.1]heptan-2-one, 1,1,2,3,3-pentamethyl-2,5,6, 7-tetrahydro-inden-4-one, 1H-3a,7-Methanoazulene, octahydro-6-methoxy-3,6,8,8-tetramethyl, [(Z)-hex-3-enyl] acetate, [(Z)-hex-3-enyl]2-hydroxybenzoate, (9Z)-cycloheptadec-9-en-1-one, chromen-2-one, cyclohexyl 2-hydroxybenzoate, ethyl 3-methyl-3-phenyloxirane-2-carboxylate, 3-ethoxy-4-hydroxybenzaldehyde, 1,4-dioxacycloheptadecane-5,17-dione, 16-oxacyclohexadecan-1-one, diethyl cyclohexane-1,4-dicarboxylate, 1-(5,5-dimethyl-1-cyclohexenyl)pent-4-en-1-one, [(2E)-3,7-dimethylocta-2,6-dienyl]acetate, 3-(1,3-benzodioxol-5-yl)-2-methylpropanal, 1,3-benzodioxole-5-carbaldehyde, 6-(pent-3-en-1-yl)tetrahydro-2H-pyran-2-one, [(1R,2S)-1-methyl-2-[[(1R,3 S,5 S)-1,2,2-trimethyl-3-bicyclo[3.1.0]hexanyl]methyl]cyclopropyl]methanol, (Z)-3,4,5,6,6-pentamethyl-hept-3-en-2-one, dodecanal, 3,7-dimethylnona-2,6-dienenitrile, (2S)-2-aminopentanedioic acid, methyl 2,4-dihydroxy-3,6-dimethylbenzoate, 2,6-dimethyloct-7-en-2-ol, 4-(4-hydroxy-4-methylpentyl)cyclohex-3-ene-1-carbaldehyde, 1-naphthalen-2-ylethanone, 4-methyl-2-(2-methylprop-1-enyl)oxane, 1H-Indene-ar-propanal, 2,3-dihydro-1,1-dimethyl-(9CI), nonanal, octanal, 2-phenylethyl 2-phenylacetate, 3-methyl-5-phenylpentan-1-ol, 4-methyl-2-(2-methylpropyl)oxan-4-ol, 1-oxacycloheptadecan-2-one, 1-(spiro[4.5]dec-7-en-7-yl)pent-4-en-1-one, 2-(4-methyl-1-cyclohex-3-enyl)propan-2-ol, 1-methyl-4-propan-2-ylidenecyclohexene, (4-methyl-1-propan-2-yl-1-cyclohex-2-enyl)acetate, 1,2-dimethylcyclohex-3-ene-1-carbaldehyde, undec-10-enal, [(4Z)-1-cyclooct-4-enyl] methyl carbonate, 8-methyl-1,5-benzodioxepin-3-one, nona-2,6-dienal, (5Z)-cyclohexadec-5-en-1-one, 2,6,10-trimethylundec-9-enal, prop-2-enyl hexanoate, (E)-1-(2,6,6-trimethyl-1-cyclohex-2-enyl)but-2-en-1-one, 3-phenylprop-2-en-1-ol, 3,7-dimethylocta-2,6-dienal, 3,7-dimethyloct-6-enyl acetate, [2-(2-methylbutan-2-yl)cyclohexyl]acetate, 3a,4,5,6,7,7a-hexahydro-4,7-methano-1H-inden-5-yl 2-methyl propanoate, 2-pentylcyclopentan-1-ol, (E)-dec-4-enal, 2-pentylcyclopentan-1-one, 2-methoxy-4-propylphenol, methyl 2-hexyl-3-oxocyclopentane-1-carboxylate, phenoxybenzene, ethyl 3-phenylprop-2-enoate, (E)-2-ethyl-4-(2,2,3-trimethyl-1-cyclopent-3-enyl)but-2-en-1-ol, 3-(4-ethylphenyl)-2,2-dimethyl-propanal, 4-methyl-2-(2-methylpropyl)oxan-4-ol, 2-methyldecanenitrile, 5-hexyloxolan-2-one, 5-(diethoxymethyl)-1,3-benzodioxole, 7-hydroxy-3,7-dimethyloctanal, (E)-4-(2,5,6,6-tetramethyl-1-cyclohex-2-enyl)but-3-en-2-one, [(1R,4S,6R)-1,7,7-trimethyl-6-bicyclo[2.2.1]heptanyl]acetate, 6-butan-2-ylquinoline, 2-methoxy-4-prop-1-en-2-ylphenol, (NE)-N-[(6E)-2,4,4,7-tetramethylnona-6,8-dien-3-ylidene] hydroxylamine, (4-propan-2-ylcyclohexyl)-methanol, 2,6-dimethylhept-5-enal, (1R,2S,5R)-5-methyl-2-propan-2-ylcyclohexan-1-ol, ethyl 2-(2-methyl-1,3-dioxolan-2-yl) acetate, 1-phenylethyl acetate, 1-(3,5,5,6,8,8-hexamethyl-6, 7-dihydronaphthalen-2-yl)ethanone, 6-butyloxan-2-one, 2,4-dimethyl-2-(5,6,7,8-tetrahydro-5,5,8,8-tetramethyl-2-naphthalenyl)-1,3-dioxolane, (2R,4S)-2-methyl-4-propyl-1, 3-oxathiane, 4-(4-hydroxyphenyl)butan-2-one, 3-methyl-5-phenylpentan-1-ol, 4-((1R,5S)-6,6-dimethylbicyclo[3.1.1] hept-2-en-2-yl)-3,3-dimethylbutan-2-one, 3-methylbut-2-enyl acetate, dec-9-en-1-ol, 5-(3-methylphenyl)pentan-1-ol, 3,7-dimethyloctan-3-ol, 1-methoxy-4-[(E)-prop-1-enyl]benzene, 4-hydroxy-3-methoxybenzaldehyde, 9-acetyl-2,6,6,8-tetramethyltricyclo(5.0.3.1.01,5)undec-8-ene, 2,5-dioxacyclohexa-decane-1,6-dione and mixtures thereof;

In one embodiment, the agent may comprise a material selected from the group consisting of a small molecule dye, a polymeric dye, a dye clay conjugate, a pigment or mixtures thereof;

In one embodiment, the agent may comprise a silicone. The silicone may comprise a material selected from the group consisting of non-functionalized siloxane polymers, functionalized siloxane polymers, silicone resins, silicone solvents, cyclic silicones and mixtures thereof.

In such embodiments, the functionalized siloxane polymers may comprise aminosilicones, amidosilicones, silicone polyethers, silicone-urethane polymers, quaternary ABn silicones, amino ABn silicones, and mixtures thereof.

In such embodiments, the non-functionalized siloxane polymer may comprise polydimethylsiloxane, dimethicone, dimethiconol, dimethicone crosspolymer, phenyl trimethicone, alkyl dimethicone, lauryl dimethicone, stearyl dimethicone, phenyl dimethicone, phenylpropyl substituted dimethicone and mixtures thereof.

In one embodiment, the silicones may comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may have a viscosity at 25 deg. C. of from about 1 cPs to about 2,000,000 cPs, or from about 5 cPs to about 800,000 cPs, or even from about 10 cPs to 300,000 cPs, or even from about 50 cPs to about 50,000 cPs. In one aspect, suitable organosilicones or mixtures thereof may have a viscosity at 25 deg. C. of from about 10 cPs to about 10,000 cPs, or from about 50 cPs to about 1,000 cPs, or even from about 80 cPs to about 600 cPs.

Silicone materials and silicone resins in particular, might conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit (CH3)3SiO0.5; D denotes the difunctional unit (CH3)2SiO; T denotes the trifunctional unit (CH3)SiO1.5; and Q denotes the quadra- or tetrafunctional unit SiO2. Primes of the unit symbols (e.g. M', D', T', and Q') denote substituents other than methyl, and must be specifically defined for each occurrence.

Suitable organosilicones may be linear, branched or cross-linked. In one aspect, the organosilicones may comprise a silicone resin. Silicone resins are highly cross-linked polymeric siloxane systems. The cross-linking is introduced through the incorporation of trifunctional and tetrafunctional silanes with monofunctional or difunctional, or both, silanes during manufacture of the silicone resin. As used herein, the nomenclature SiO"n"/2 represents the ratio of oxygen and silicon atoms. For example, SiO1/2 means that one oxygen is shared between two Si atoms. Likewise SiO2/2 means that two oxygen atoms are shared between two Si atoms and SiO3l2 means that three oxygen atoms are shared are shared between two Si atoms.

In one aspect, the organosilicone may comprise polydimethylsiloxane, dimethicone, dimethiconol, dimethicone crosspolymer, phenyl trimethicone, alkyl dimethicone, lauryl dimethicone, stearyl dimethicone, phenyl dimethicone, phenylpropyl substituted dimethicone and mixtures thereof.

In one aspect, the organosilicone may comprise a cyclic silicone. The cyclic silicone may comprise a cyclomethicone of the formula [(CH3)2SiO]n where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and mixtures thereof.

Non-limiting examples of suitable silicones are Pulpaid (Registered trademark) 3500, Pulpaid (Registered trademark) 3600, Xiameter (Registered trademark) ACP-0001, Xiameter (Registered trademark) PMX-0245 and Xiameter (Registered trademark) PMX-0246, Dow Corning (Registered trademark) FS1266 from Dow Corning; Silfoam (Registered trademark) SD 860, Silfoam (Registered trademark) SD 168, Silfoam (Registered trademark) SD 850, Silfoam (Registered trademark) SD 650, Silfoam (Registered trademark) SE 36, Silfoam (Registered trademark) SE 39, Silfoam (Registered trademark) SC 1092, Silfoam (Registered trademark) SC 1132, Silfoam (Registered trademark) SC 129, Silfoam (Registered trademark) SC 132, Silfoam (Registered trademark) SE 47, Silfoam (Registered trademark) SRE and Silfoam (Registered trademark) SE 90, from Wacker Corp.; Tego 3062 from Goldschmidt; AF-140TG and Tri-Lube-60-PR from Tri-Chem Industries; and Antifoam 2226 from Basildon Chemicals.

In one embodiment, the agent may be selected from mineral oils, soybean oils, petrolatum, and lanolin. In one embodiment, the agent may include sensates. Exemplary sensates include a composition of menthol and menthyl lactate.

Additional exemplary benefit agents are described in patent application publication 2014/0342972, "Encapsulate" published Nov. 20, 2014 and incorporated herein, in its entirety, by reference.

In certain aspects, the entities may be contained within a fluid within the microparticles. The fluid may be any suitable fluid that can contain the entities, e.g., suspended within the fluid. In some cases, the fluid may be immiscible with the fluids forming the entities, e.g., where the entities comprise fluids. Non-limiting examples of suitable fluids include water or other aqueous fluids (such as cell or biological media, salt solutions, alcohol, etc.), or hydrophobic fluids. Examples of hydrophobic liquids include, but are not limited to, oils such as hydrocarbons, silicone oils, mineral oils, fluorocarbon oils, organic solvents etc.

In certain embodiments, the fluid may be one in which the agent within the entities does not easily dissolve or other pass through, e.g., to reach the shell of the microparticle. If the agent has relatively low solubility within the fluid, then relatively large amounts or concentrations of agent may be contained within the entities, relative to the fluid. Thus, for example, even if there is a relatively low concentration of agent that can be contained within the fluid, the microparticle may exhibit surprisingly high amounts of the agent therein, if one were to assume that the microparticle were only filled with the fluid. In addition, in some cases, the rate-limiting step for the release of agent from the microparticle may be controlled by the rate of dissolution of the agent within the fluid, rather than by the maximum concentration of agent within the fluid, since much of the agent may be stored within the entities instead of within the fluid itself.

As used herein, two fluids are immiscible, or not miscible, with each other when one is not soluble in the other to a level of at least 10% by weight at the temperature and under the conditions at which the emulsion is produced. For instance, two fluids may be selected to be immiscible within the time frame of the formation of the fluidic droplets.

The microparticle may also contain a shell surrounding the fluid and the entities, in certain aspects. The shells can comprise a polymer in some embodiments. Examples include, but are not limited to, ethoxylated trimethylolpropane triacrylate (ETPTA), polystyrene, polycaprolactone, polyisoprene, poly(lactic acid), polystyrene (PS), polycaprolactone (PCL), polyisoprene (PIP), poly(lactic acid), polyethylene, polypropylene, polyacrylonitrile, polyimide, polyamide, poly(normal-butyl acrylate)-poly(acrylic acid), and/or mixtures and/or co-polymers of these and/or other polymers.

In one embodiment, the shell material may comprise, poly(vinyl alcohol), poly(vinyl acetate), poly(vinyl pyrrolidone), poly(vinyl acetate phthalate), vinyl acetate neodecanoic acid co-polymer, vinyl acetate ethylene co-polymer, vinyl acetate crotonic acid neodecanoate co-polymer, vinyl acetate crotonic acid co-polymer, vinyl acetate butyl maleate co-polymer, cellulose acetate, cellulose acetate phthalate, ethyl cellulose, hydroxyl propyl methyl cellulose phathalate, cellulose acetate butyrate, vinyl pyrrolidone vinyl acetate co-polymer, poly(styrene-co-maleic acid) isobutyl ester, poly (styrene-co-butadiene), poly(styrene-co-acrylic) and mixtures thereof.

Further non-limiting examples of shell materials may comprise Vinavil® VIN, Vinavil® 6915, Vinavil® 03V, Vinavil EVA® 04 and Vinaflex® CR50 from Vinavil S.p.A., Italy; Luviset® CAN, Luviset® CA66 and Luviskol® VA 37 E from BASF, Germany; Sureteric® and Ethocel, Et from Colorcon, U.S.A.; Mowiol® grades from Sigma-Aldrich; Antaron-Ganex® V-220 F and Antaron-Ganex® WP-660 from ISP Chemicals, or mixtures thereof. [0052] In one aspect, said core and/or said shell may comprise a viscosity regulator. [0053] In one aspect, said viscosity regulator may comprise a water-soluble solvent, a water-insoluble solvent, silicones, perfume raw materials and/or mixtures thereof.

The microparticles described herein may have any suitable average cross-sectional diameter. Those of ordinary skill in the art will be able to determine the average cross-sectional diameter of a single and/or a plurality of particles, for example, using laser light scattering, microscopic examination, or other known techniques. The average cross-sectional diameter of a single particle, in a non-spherical particle, is the diameter of a perfect sphere having the same volume as the non-spherical particle. The average cross-sectional diameter of a particle (and/or of a plurality or series of particles or droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers, or between about 50 micrometers and about 1 mm, between about 10 micrometers and about 500 micrometers, or between about 50 micrometers and about 100 micrometers in some cases. The average cross-sectional diameter may also be at least about 1 micrometer, at least about 2 micrometers, at least about 3 micrometers, at least about 5 micrometers, at least about 10 micrometers, at least about 15 micrometers, or at least about 20 micrometers in certain cases. In some embodiments, at least about 50%, at least about 75%, at least about 90%, at least about 95%, or at least about 99% of the particles or droplets within a plurality of particles or droplets has an average cross-sectional diameter within any of the ranges outlined in this paragraph.

Certain applications may use a plurality of particles, at least some of which contain a fluid and entities such as those described herein. Some embodiments of the invention advantageously employ microparticles with relatively consistent properties. For example, in some embodiments, a plurality of particles is provided wherein the distribution of thicknesses of the outermost layer among the plurality of particles is relatively uniform. In some embodiments, a plurality of particles is provided having an overall thickness, measured as the average of the average thicknesses of each of the plurality of particles. In some cases, the distribution of the average thicknesses can be such that no more than about 5%, no more than about 2%, or no more than about 1% of the particles or droplets have an outermost layer with an average thickness thinner than 90% (or thinner than 95%, or thinner than 99%) of the overall average thickness and/or thicker than 110% (or thicker than 105%, or thicker than about 101%) of the overall average thickness of the outermost layer.

In one embodiment, the microparticles may comprise relatively thick shells. Exemplary shell thicknesses for such embodiments include thicknesses ranging from between about 0.1 µm to about 10 µm. In such embodiments, the shell wall thicknesses of a population of the particles may have a mean of between about wtmm µm to about wthmM µm.

In one set of embodiments, the microparticles may comprise relatively thin outer shells. Techniques for forming relatively thin outer shells include those discussed in U.S. Provisional Application Ser. No. 61/980,541, filed Apr. 16, 2014, entitled "Systems and Methods for Producing Droplet Emulsions with Relatively Thin Shells"; or in U.S. Pat. Apl. Pub. No. 2014-0220350, entitled "Multiple Emulsions and Techniques for the Formation of Multiple Emulsions," published Aug. 7, 2014, each incorporated herein by reference in its entirety.

Thus, in some embodiments, the shell may have an average thickness (i.e., between the first fluid and the second fluid) of less than about 1 micrometer, less than about 500 nm, less than about 300 nm, less than about 200 nm, less than about 100 nm, less than about 50 nm, less than about 30 nm, less than about 20 nm, or less than about 10 nm. The thickness may be determined optically or visually, or in some cases, estimated based on the volumes and/or flow rates of fluid entering or leaving a conduit. If the droplet is non-spherical, then average thickness or diameters may be determined using the diameter of a perfect sphere having the same volume as the non-spherical droplet(s).

The volumes or thicknesses of a layer of fluid in a droplet may be determined or estimated (e.g., before and/or after distortion) using any suitable technique, e.g., visually or optically. In some cases, the volumes or thickness of a layer of fluid may be estimated statistically, e.g., by determining the amount of fluid present in the microparticles.

In addition, in some embodiments, the thickness may be determined as a percentage of the diameter of the overall droplet within the carrying fluid. For example, the thickness of the shell of the microparticle may be than about 20%, less than about 15%, less than about 10%, less than about 5%, less than about 3%, less than about 1%, less than about 0.5%, less than about 0.3%, or less than about 0.1% of the diameter of the overall droplet.

In addition, in some embodiments, the shell may comprise a relatively small percentage by volume of the overall microparticle. For example, the shell may comprise less than about 20%, less than about 15%, less than about 10%, less than about 5%, less than about 3%, less than about 1%, less than about 0.5%, less than about 0.3%, or less than about 0.1% of the overall droplet. In another set of embodiments, the shell may have a thickness such that the difference between the average diameter of the shell and the average diameter of the interior of the shell (including fluid and any entities therein) is less than about 20% of the average diameter of the overall droplet, and in some cases, less than about 15%, less than about 10%, less than about 5%, less than about 3%, less than about 1%, less than about 0.5%, less than about 0.3%, or less than about 0.1% of the average diameter of the overall microparticle.

In some embodiments, the shell may have an average thickness of less than about 0.05, less than about 0.01, less than about 0.005, or less than about 0.001 times the average cross-sectional diameter of the microparticle, or between about 0.0005 and about 0.05, between about 0.0005 and about 0.01, between about 0.0005 and about 0.005, or between about 0.0005 and about 0.001 times the average cross-sectional diameter of the microparticle. In some embodiments, the shell may have an average thickness of less than about 1 micron, less than about 500 nm, or less than about 100 nm, or between about 50 nm and about 1 micron, between about 50 nm and about 500 nm, or between about 50 nm and about 100 nm. One of ordinary skill in the art would be capable of determining the average thickness of the shell, for example, by examining scanning electron microscope (SEM) images of the microparticle.

It should also be understood that in some cases, the interior of the shell (including fluid and any entities therein) is relatively large, e.g., a large percentage of the volume of the microparticle is taken up by the interior, which may result in the shell having a relatively thin thickness. Thus, for example, on a volume basis, the interior may take up at least about 80% of the volume of the microparticle, and in some cases, at least about 85%, at least about 90%, at least about 95%, at least about 97%, at least about 98%, at least about 99%, at least about 99.5%, or at least about 99.7% of the volume of the microparticle. In some cases, the diameter of the interior may be at least about 80% of the diameter of the microparticle, and in some cases, at least about 85%, at least about 90%, at least about 95%, at least about 97%, at least about 98%, at least about 99%, at least about 99.5%, or at least about 99.7% of the diameter of the microparticle.

In one set of embodiments, the interior comprises at least about 50% of the volume of the microparticle, and in some cases, at least about 60%, at least about 70%, at least about 75%, at least about 80%, or at least about 85% of the volume of the microparticle. In some cases, the volume of the interior may also be no more than about 90%, no more than about 85%, no more than about 80%, no more than about 75%, no more than about 70%, no more than about 65%, no more than about 60%, or no more than about 55% of the volume of the microparticle. Combinations of any of these are also possible, e.g., the interior may comprise between about 50% and about 80% of the volume of the microparticle.

The microparticles may have relatively uniform cross-sectional diameters in certain embodiments. The use of particles with relatively uniform cross-sectional diameters can allow one to control viscosity, the amount of species delivered to a target, and/or other parameters of the delivery of fluid and/or species from the particles. In some embodiments, the particles are relatively monodisperse, or the plurality of particles has an overall average diameter and a distribution of diameters such that no more than about 5%, no more than about 2%, or no more than about 1% of the particles or droplets have a diameter less than about 90% (or less than about 95%, or less than about 99%) and/or greater than about 110% (or greater than about 105%, or greater than about 101%) of the overall average diameter of the plurality of particles.

In some embodiments, the microparticles has an overall average diameter and a distribution of diameters such that the coefficient of variation of the cross-sectional diameters of the particles or droplets is less than about 10%, less than about 5%, less than about 2%, between about 1% and about 10%, between about 1% and about 5%, or between about 1% and about 2%. The coefficient of variation can be determined by those of ordinary skill in the art, and may be defined as:

$$c_V = \frac{\sigma}{|\mu|}$$

wherein $\sigma$ is the standard deviation and $\mu$ is the mean.

In some aspects, the microparticles may be exposed to an environment to which the agent is to be released. The environment may be any suitable environment, and can be, e.g., a liquid or a gas. The agent may be releasable from the microparticles, in some embodiment, without significantly damaging or disrupting the microparticles, e.g., by damaging the shell of the microparticles to cause release of the agent. Thus, for instance, the agent may be diffuse across the outer shell of the microparticles to be released externally of the microparticles.

The agent may exit the microparticles passively, or the microparticles may be treated in some way to cause release of the agent. For instance, in one set of embodiments, the agent may be released by agitating the microparticles, e.g., intermittently or continuously. In another set of embodiments, the microparticles may be exposed to a fluid, such as oil or water. For example the agent may be soluble in oil or water, such that upon reaching the surface of the microparticle, the agent can readily enter the fluid.

In some embodiments, relatively high amounts of agent may be released from the microparticles into the surrounding environment, e.g., without damaging the microparticles. For instance, at least about 30 wt %, at least about 50 wt %, at least about 60 wt %, at least about 70 wt %, at least about 75 wt %, at least about 80 wt %, at least about 85 wt %, at least about 90 wt %, or at least about 95 wt % of the agent may be released from the microparticles upon exposure to a suitable surrounding environment.

As mentioned, in accordance with certain embodiments, the rate of release of agent from the microparticles may be controlled, e.g., based on the ability of the agent to exit the entities contained within the microparticles and pass through the internal fluid and the shell of the microparticles. Thus, as discussed herein, the amount of loading of entities within the microparticles, and the rate at which the agent is released from the microparticles, may not necessarily be coupled to each other. Thus, for example, the fluid surrounding the entities may act as a rate-limiting step (e.g., if the agent is not fully soluble within the fluid), and the entities may thus act as a "reservoir" to contain the agent prior to release from the microparticles.

Some aspects of the present invention are generally directed to systems and methods for forming such microparticles. In one set of embodiments, for example, various microfluidic conduits can be positioned to create the multiple emulsion droplets, e.g., in series. In some cases, e.g., by controlling the flow of a fluid through a conduit, surprisingly thin inner layers of fluid may be created.

In one set of embodiments, a first conduit may be used to inject a first fluid into a second fluid that is immiscible with the first fluid. The first fluid may contain entities therein, e.g. suspended therein. The first fluid may comprise an emulsion having continuous and dispersed phases. The dispersed phase may be immiscible in the continuous phase but substantially miscible in the second fluid, or polymers which may be formed from the second fluid. In some cases, the entities may also contain an agent for subsequent release from the microparticles. The entities may be contained within the first fluid in any suitable amount or concentration, including those described above with respect to the final amount or concentration within the microparticles.

The first conduit may end at an exit opening. The first conduit may gradually or suddenly reach the diameter of the exit opening. In one set of embodiments, a tapered region may be used. The length of the tapered region may be any suitable length as determined in the direction of average fluid flow within the channel; for example, the length can be less than about 1 mm, less than about 500 micrometers, less than about 300 micrometers, less than about 100 micrometers, less than about 50 micrometers, less than about 30 micrometers, less than about 10 micrometers, etc.

In some embodiments, the first conduit may have a cross-sectional dimension of less than about 1 mm, less than about 500 micrometers, less than about 200 micrometers, less than about 100 micrometers, less than about 75 micrometers, less than about 50 micrometers, or other dimensions as discussed herein. In some cases, the cross-sectional area of the first conduit may vary. In some cases, the first conduit is substantially smaller than the second conduit at the point where the first conduit opens into a second conduit. For instance, the first conduit may have a cross-sectional area of the exit opening that is no more than about 75%, no more than about 50%, no more than about 45%, no more than about 40%, no more than about 35%, no more than about 30%, no more than about 25%, no more than about 20%, no more than about 15%, no more than about 10%, or no more than about 5% of the cross-sectional area of the second conduit at that location.

Upon exiting the exit opening of the first conduit, the first fluid (containing entities, e.g., as discussed above) may encounter a second fluid and a third fluid contained within a second conduit. The second fluid may be immiscible with the first fluid and/or the third fluid, in some cases. Thus, the second fluid may be caused to form droplets surrounding the first fluid (and entities) contained within the third fluid. The second and third fluids may be introduced into the second conduit in directions substantially opposed to each other. The droplets may be formed prior to entering the third conduit or while the combination of fluids is passing through the third conduit.

In some embodiments, the second conduit may have a cross-sectional dimension of less than about 1 mm, less than about 500 micrometers, less than about 200 micrometers, less than about 100 micrometers, less than about 75 micrometers, less than about 50 micrometers, or other dimensions as discussed herein. The cross-sectional area of the second conduit may be substantially constant, or may vary. For instance, the second conduit may be tapered.

The droplets may then exit the second conduit through an entrance opening of a third conduit, e.g., to be polymerized, or for subsequent use, etc. Thus, for example, one or more of the fluids may be hardened as discussed below to form a particle. The particle may have the same dimensions as the droplet prior to hardening.

In some embodiments, the third conduit may have a cross-sectional dimension of less than about 1 mm, less than about 500 micrometers, less than about 200 micrometers, less than about 100 micrometers, less than about 75 micrometers, less than about 50 micrometers, or other dimensions as discussed herein. The cross-sectional area of the third conduit may be substantially constant, or may vary. For instance, the third conduit may be tapered. In some cases, the third conduit is substantially smaller than the second conduit at the entrance opening to the third conduit. For instance, the third conduit may have a cross-sectional area of the exit opening that is no more than about 75%, no more than about 50%, no more than about 45%, no more than about 40%, no more than about 35%, no more than about 30%, no more than about 25%, no more than about 20%, no more than about 15%, no more than about 10%, or no more than about 5% of the cross-sectional area of the third conduit at that location. In some cases, the third conduit may have a diameter that changes moving away from the entrance opening, although in other cases, the diameter of the third conduit may be substantially constant.

Some benefit agents and/or shell material solutions might have a high viscosity after dissolution or dispersion, so certain additives as viscosity regulators might be added to the core and/or the shell as processing aid to facilitate the flow of such benefit agents and/or shell materials through the conduits. Such viscosity regulators may comprise water-soluble solvents, water-insoluble solvents, perfume raw materials, silicones and/or mixtures thereof. Non-limiting examples include ethanol, propanol, isopropanol, n-propanol, n-butanol, t-butanol, propylene glycol, 1,3-propanediol, ethylene glycol, diethylene glycol, dipropylene glycol, 1,2,3-propanetriol, propylene carbonate, phenylethyl alcohol, 2-methyl 1,3-propanediol, hexylene glycol, glycerol, sorbitol, polyethylene glycols, 1,2-hexanediol, 1,2-pentanediol, 1,2-butanediol, 1,4 butanediol, 1,4-cyclohexanedimethanol, pinacol, 1,5-hexanediol, 1,6-hexanediol, 2,4-dimethyl-2,4-pentanediol, 2,2,4-trimethyl-1,3-pentanediol (and ethoxylates), 2-ethyl-1,3-hexanediol, phenoxyethanol (and ethoxylates), glycol ethers such as butyl carbitol and dipropylene glycol n-butyl ether, ester solvents such as dimethyl esters of adipic, glutaric, and succinic acids, hydrocarbons such as decane and dodecane, camethylcyclopentasiloxane, cyclohexasiloxane, ethyl-2-methylbutanoate, ethyl-2-methylbutyrate, isopropyl myristate, thyl-2-methyl pentanoate, hexyl acetate, allyl caproate and mixtures thereof.

In one set of embodiments, the outer, second fluid surrounding the droplets may be hardened to form microparticles, e.g., containing the first fluid and the entities. For instance, in one set of embodiments, light, such as ultraviolet light, may be used to facilitate polymerization of a polymer. In another set of embodiments, the third fluid may contain a chemical that can react with the second fluid (e.g., at its surface) to harden the second fluid. In yet another set of embodiments, certain changes, such as temperature changes, may be used to induce hardening of the second fluid to form microparticles.

For example, in some embodiments, a fluid may be dried, gelled, and/or polymerized, and/or otherwise solidified, e.g., to form a solid, or at least a semi-solid. The solid that is formed may be rigid in some embodiments, although in other cases, the solid may be elastic, rubbery, deformable, etc. In some cases, for example, an outermost layer of fluid may be solidified to form a solid shell at least partially containing an interior containing a fluid and/or a species. Any technique able to solidify at least a portion of a fluidic droplet can be used. For example, in some embodiments, a fluid within a fluidic droplet may be removed to leave behind a material (e.g., a polymer) capable of forming a solid shell. In other embodiments, a fluidic droplet may be cooled to a temperature below the melting point or glass transition temperature of a fluid within the fluidic droplet, a chemical reaction may be induced that causes at least a portion of the fluidic droplet to solidify (for example, a polymerization reaction, a reaction between two fluids that produces a solid product, etc.), or the like. Other examples include pH-responsive or molecular-recognizable polymers, e.g., materials that gel upon exposure to a certain pH, or to a certain species. In some embodiments, a fluidic droplet is solidified by increasing the temperature of the fluidic droplet. For instance, a rise in temperature may drive out a material from the fluidic droplet (e.g., within the outermost layer of a multiple emulsion droplet) and leave behind another material that forms a solid. Thus, in some cases, an outermost layer of a multiple emulsion droplet may be solidified to form a solid shell that encapsulates entities contained within a fluid.

In one embodiment, for light curable wall materials such as acrylate and acrylamide based monomer/oligomers, photoinitiators may include benzyl ketones, monomeric hydroxyl ketones, polymeric hydroxyl ketones, alpha-amino ketones, acyl phosphine oxides, metallocenes, benzophenone, benzophenone derivatives, and many others as described in (US 20140261508 A1),
Exemplary photoinitiators include: Benzoin Ethyl Ether, 2-hydroxy-2-Methylphenylpropanone, Irgacure 369, Irgacure LEX 201, Irgacure 819, Darocur 4265, Irgacure 184, Irgacure 2959, and the visible light initiator: Irgacure 784, Camphorquinone(GENOCURE*CQ).

Acrylate and acrylamide can also be cured thermally by adding thermal initiator as described in patent publication: WO 2011084141 A2(Appleton). The initiators are energy activated meaning free radicals are generated when the initiators are subjected to heat or other energy input.

Exemplary initiators include peroxy initiators, azo initiators, peroxides, and compounds such as 2,2'-azobismethylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2, 2'-azobis (isobutylnitrile), 2,2'-azobis(2,4-dimethylpentanenitrile), 2,2'-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1'-azobis(cyanocyclohexane), benzoyl peroxide, decanoyl peroxide; lauroyl peroxide; benzoyl peroxide, di(n-propyl) peroxydicarbonate, di(sec-butyl) peroxydicarbonate, di(2-ethylhexyl) peroxydicarbonate, 1,1-dimethyl-3-hydroxybutyl peroxyneodecanoate, a-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di-t-amyl peroxide, 2,5-dimethyl-2,5-di-(t-butylperoxy) hexyne-3, cumene hydroperoxide, 1,1-di-(t-butylperoxy)-3, 3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like. Blends of initiators can also be employed.

Commercially available initiators, such as Vazo initiators, typically indicate a decomposition temperature for the initiator. In one embodiment, the initiator is selected to have a decomposition point of about 50° C. or higher. Multiple initiators may be employed, either as a blend in the oil phase, or in either of the oil or water phases. In one embodiment, initiators are selected to stagger the decomposition temperatures at the various steps, pre-polymerization, wall formation and hardening or polymerizing of the capsule wall material. For example, a first initiator in the oil phase can decompose at 55° C., to promote prepolymer formation; a second can decompose at 60° C. to aid forming the wall material. Optionally a third initiator can decompose at 65° C. to facilitate polymerization of the capsule wall material. The total amount of initiator can be typically as low as 0.1 weight percent or as high as 10 weight percent.

In certain aspects of the present invention, as discussed, the microparticles are prepared in a microfluidic system. "Microfluidic," as used herein, refers to a device, apparatus, or system including at least one fluid channel having a cross-sectional dimension of less than about 1 millimeter (mm), and in some cases, a ratio of length to largest cross-sectional dimension of at least 3:1. One or more channels of the system may be a capillary tube. In some cases, multiple channels are provided, and in some embodiments, at least some are nested, as described herein. The channels may be in the microfluidic size range and may have, for example, average inner diameters, or portions having an inner diameter, of less than about 1 millimeter, less than about 300 micrometers, less than about 100 micrometers, less than about 30 micrometers, less than about 10 micrometers, less than about 3 micrometers, or less than about 1 micrometer, thereby providing droplets having comparable average diameters. The cross-section of one or more of the channels may, have a height that is substantially the same as a width at the same point. In cross-section, the channels may be rectangular or substantially non-rectangular, such as circular or elliptical.

As used herein, the term "fluid" generally refers to a substance that tends to flow and to conform to the outline of its container, i.e., a liquid, a gas, a viscoelastic fluid, etc. In one embodiment, the fluid is a liquid. Typically, fluids are materials that are unable to withstand a static shear stress, and when a shear stress is applied, the fluid experiences a continuing and permanent distortion. The fluid may have any suitable viscosity that permits flow. If two or more fluids are present, each fluid may be independently selected among essentially any fluids (liquids, gases, and the like) by those of ordinary skill in the art, by considering the relationship between the fluids.

A variety of materials and methods, according to certain aspects of the invention, can be used to form articles or components such as those described herein, e.g., channels such as microfluidic channels, chambers, etc. For example, various articles or components can be formed from solid materials, in which the channels can be formed via micromachining, film deposition processes such as spin coating and chemical vapor deposition, laser fabrication, photolithographic techniques, etching methods including wet chemical or plasma processes, 3D printing, and the like. See, for example, *Scientific American,* 248:44-55, 1983 (Angell, et al).

In one set of embodiments, various structures or components of the articles described herein can be formed from glass or a polymer, for example, an elastomeric polymer such as polydimethylsiloxane ("PDMS"), polytetrafluoroethylene ("PTFE" or Teflon®), epoxy, norland optical adhesive, or the like. For instance, according to one embodiment, microfluidic channels may be formed from glass tubes or capillaries. In addition, in some cases, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E.

Ingber, published in the *Annual Review of Biomedical Engineering*, 2001, Vol. 3, pages 335-373; each of these references is incorporated herein by reference). In addition, in some embodiments, various structures or components of the articles described herein can be formed of a metal, for example, stainless steel.

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various structures or components of the article are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, dodecyltrichlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of various structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour, about 3 hours, about 12 hours, etc. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures or channels from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, structures can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable or bonded to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material, e.g., as discussed herein. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device. A non-limiting example of such a coating is disclosed below; additional examples are disclosed in Int. Pat. Apl. Ser. No. PCT/US2009/000850, filed Feb. 11, 2009, entitled "Surfaces, Including Microfluidic Channels, With Controlled Wetting Properties," by Weitz, et al., published as WO 2009/120254 on Oct. 1, 2009, incorporated herein by reference.

In some embodiments, certain microfluidic structures of the invention (or interior, fluid-contacting surfaces) may be formed from certain oxidized silicone polymers. Such surfaces may be more hydrophilic than the surface of an elastomeric polymer. Such hydrophilic surfaces can thus be more easily filled and wetted with aqueous solutions.

In some embodiments, a bottom wall of a microfluidic device of the invention is formed of a material different from one or more side walls or a top wall, or other components. For example, in some embodiments, the interior surface of a bottom wall comprises the surface of a silicon wafer or microchip, or other substrate. Other components may, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques may be used, as would be apparent to those of ordinary skill in the art, including, but not limited to, the use of separate adhesives, bonding, solvent bonding, ultrasonic welding, etc.

Thus, in certain embodiments, the design and/or fabrication of the article may be relatively simple, e.g., by using relatively well-known soft lithography and other techniques such as those described herein. In addition, in some embodiments, rapid and/or customized design of the article is possible, for example, in terms of geometry. In one set of embodiments, the article may be produced to be disposable, for example, in embodiments where the article is used with substances that are radioactive, toxic, poisonous, reactive, biohazardous, etc., and/or where the profile of the substance (e.g., the toxicology profile, the radioactivity profile, etc.) is unknown. Another advantage to forming channels or other structures (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one set of embodiments, one or more of the channels within the device may be relatively hydrophobic or relatively hydrophilic, e.g. inherently, and/or by treating one or more of the surfaces or walls of the channel to render them more hydrophobic or hydrophilic. Generally, the fluids that are formed into droplets in the device are substantially immiscible, at least on the time scale of forming the droplets, and the fluids will often have different degrees of hydrophobicity or hydrophilicity. Thus, for example, a first fluid may be more hydrophilic (or more hydrophobic) relative to a second fluid, and the first and the second fluids may be substantially immiscible. Thus, the first fluid can from a discrete droplet within the second fluid, e.g., without substantial mixing of the first fluid and the second fluid (although some degree of mixing may nevertheless occur under some conditions). Similarly, the second fluid may be more hydrophilic (or more hydrophobic) relative to a third fluid (which may be the same or different than the first fluid), and the second and third fluids may be substantially immiscible.

Accordingly, in some cases, a surface of a channel may be relatively hydrophobic or hydrophilic, depending on the fluid contained within the channel. In one set of embodiments, a surface of the channel is hydrophobic or hydrophilic relative to other surfaces within the device. In addition, in some embodiments, a relatively hydrophobic surface may exhibit a water contact angle of greater than about 90°, and/or a relatively hydrophilic surface may exhibit a water contact angle of less than about 90°.

In some cases, relatively hydrophobic and/or hydrophilic surfaces may be used to facilitate the flow of fluids within the channel, e.g., to maintain the nesting of multiple fluids within the channel in a particular order.

In some aspects, as previously discussed, emulsions such as those described herein may be prepared by controlling the hydrophilicity and/or hydrophobicity of the channels used to form the emulsion. In one set of embodiments, the hydrophilicity and/or hydrophobicity of the channels may be controlled by coating a sol-gel onto at least a portion of a channel. For instance, in one embodiment, relatively hydrophilic and relatively hydrophobic portions may be created by applying a sol-gel to portions of the channel surfaces, which renders those portions relatively hydrophobic. The sol-gel may comprise an initiator, such as a photoinitiator. Portions (e.g., channels, and/or portions of channels) may be rendered relatively hydrophilic by filling the channels with a solution containing a hydrophilic moiety (for example, acrylic acid), and exposing the portions to a suitable trigger for the initiator (for example, light or ultraviolet light in the case of a photoinitiator). For example, the portions may be exposed by using a mask to shield portions in which no reaction is desired, by directing a focused beam of light or heat onto the portions in which reaction is desired, or the like. In the exposed portions, the initiator may cause the reaction (e.g., polymerization) of the hydrophilic moiety to the sol-gel, thereby rendering those portions relatively hydrophilic (for instance, by causing poly(acrylic acid) to become grafted onto the surface of the sol-gel coating in the above example).

As is known to those of ordinary skill in the art, a sol-gel is a material that can be in a sol or a gel state, and typically includes polymers. The gel state typically contains a polymeric network containing a liquid phase, and can be produced from the sol state by removing solvent from the sol, e.g., via drying or heating techniques. In some cases, the sol may be pretreated before being used, for instance, by causing some polymerization to occur within the sol.

In some embodiments, the sol-gel coating may be chosen to have certain properties, for example, having a certain hydrophobicity. The properties of the coating may be controlled by controlling the composition of the sol-gel (for example, by using certain materials or polymers within the sol-gel), and/or by modifying the coating, for instance, by exposing the coating to a polymerization reaction to react a polymer to the sol-gel coating, as discussed below.

For example, the sol-gel coating may be made more hydrophobic by incorporating a hydrophobic polymer in the sol-gel. For instance, the sol-gel may contain one or more silanes, for example, a fluorosilane (i.e., a silane containing at least one fluorine atom) such as heptadecafluorosilane, or other silanes such as methyltriethoxy silane (MTES) or a silane containing one or more lipid chains, such as octadecylsilane or other $CH_3(CH_2)_n$— silanes, where n can be any suitable integer. For instance, n may be greater than 1, 5, or 10, and less than about 20, 25, or 30. The silanes may also optionally include other groups, such as alkoxide groups, for instance, octadecyltrimethoxysilane. In general, most silanes can be used in the sol-gel, with the particular silane being chosen on the basis of desired properties such as hydrophobicity. Other silanes (e.g., having shorter or longer chain lengths) may also be chosen in other embodiments of the invention, depending on factors such as the relative hydrophobicity or hydrophilicity desired. In some cases, the silanes may contain other groups, for example, groups such as amines, which would make the sol-gel more hydrophilic. Non-limiting examples include diamine silane, triamine silane, or N-[3-(trimethoxysilyl)propyl] ethylene diamine silane. The silanes may be reacted to form oligomers or polymers within the sol-gel, and the degree of polymerization (e.g., the lengths of the oligomers or polymers) may be controlled by controlling the reaction conditions, for example by controlling the temperature, amount of acid present, or the like. In some cases, more than one silane may be present in the sol-gel. For instance, the sol-gel may include fluorosilanes to cause the resulting sol-gel to exhibit greater hydrophobicity, and other silanes (or other compounds) that facilitate the production of polymers. In some cases, materials able to produce $SiO_2$ compounds to facilitate polymerization may be present, for example, TEOS (tetraethyl orthosilicate).

It should be understood that the sol-gel is not limited to containing only silanes, and other materials may be present in addition to, or in place of, the silanes. For instance, the coating may include one or more metal oxides, such as $SiO_2$, vanadia ($V_2O_5$), titania ($TiO_2$), and/or alumina ($Al_2O_3$).

In some instances, the microfluidic channel is present in a material suitable to receive the sol-gel, for example, glass, metal oxides, or polymers such as polydimethylsiloxane (PDMS) and other siloxane polymers. For example, in some cases, the microfluidic channel may be one which contains silicon atoms, and in certain instances, the microfluidic channel may be chosen such that it contains silanol (Si—OH) groups, or can be modified to have silanol groups. For instance, the microfluidic channel may be exposed to an oxygen plasma, an oxidant, or a strong acid to cause the formation of silanol groups on the microfluidic channel.

The sol-gel may be present as a coating on the microfluidic channel, and the coating may have any suitable thickness. For instance, the coating may have a thickness of no more than about 100 micrometers, no more than about 30 micrometers, no more than about 10 micrometers, no more than about 3 micrometers, or no more than about 1 micrometer. Thicker coatings may be desirable in some cases, for instance, in applications in which higher chemical resistance is desired. However, thinner coatings may be desirable in other applications, for instance, within relatively small microfluidic channels.

In one set of embodiments, the hydrophobicity of the sol-gel coating can be controlled, for instance, such that a first portion of the sol-gel coating is relatively hydrophobic, and a second portion of the sol-gel coating is relatively hydrophilic. The hydrophobicity of the coating can be determined using techniques known to those of ordinary skill in the art, for example, using contact angle measurements such as those discussed herein. For instance, in some cases, a first portion of a microfluidic channel may have a hydrophobicity that favors an organic solvent to water, while a second portion may have a hydrophobicity that favors water to the organic solvent. In some cases, a hydrophilic surface is one that has a water contact angle of less than about 90° while a hydrophobic surface is one that has a water contact angle of greater than about 90°.

The hydrophobicity of the sol-gel coating can be modified, for instance, by exposing at least a portion of the sol-gel coating to a polymerization reaction to react a polymer to the sol-gel coating. The polymer reacted to the sol-gel coating may be any suitable polymer, and may be chosen to have certain hydrophobicity properties. For instance, the polymer may be chosen to be more hydrophobic or more hydrophilic than the microfluidic channel and/or the sol-gel coating. As an example, a hydrophilic polymer that could be used is poly(acrylic acid).

The polymer may be added to the sol-gel coating by supplying the polymer in monomeric (or oligomeric) form to the sol-gel coating (e.g., in solution), and causing a polymerization reaction to occur between the polymer and the sol-gel. For instance, free radical polymerization may be used to cause bonding of the polymer to the sol-gel coating. In some embodiments, a reaction such as free radical polymerization may be initiated by exposing the reactants to heat and/or light, such as ultraviolet (UV) light, optionally in the presence of a photoinitiator able to produce free radicals (e.g., via molecular cleavage) upon exposure to light. Those of ordinary skill in the art will be aware of many such photoinitiators, many of which are commercially available, such as Irgacur 2959 (Ciba Specialty Chemicals) or 2-hydroxy-4-(3-triethoxysilylpropoxy)-diphenylketone (SIH6200.0, ABCR GmbH & Co. KG).

The photoinitiator may be included with the polymer added to the sol-gel coating, or in some cases, the photoinitiator may be present within the sol-gel coating. For instance, a photoinitiator may be contained within the sol-gel coating, and activated upon exposure to light. The photoinitiator may also be conjugated or bonded to a component of the sol-gel coating, for example, to a silane. As an example, a photoinitiator such as Irgacur 2959 may be conjugated to a silane-isocyanate via a urethane bond, where a primary alcohol on the photoinitiator may participate in nucleophilic addition with the isocyanate group, which may produce a urethane bond.

It should be noted that only a portion of the sol-gel coating may be reacted with a polymer, in some embodiments of the invention. For instance, the monomer and/or the photoinitiator may be exposed to only a portion of the microfluidic channel, or the polymerization reaction may be initiated in only a portion of the microfluidic channel. As a particular example, a portion of the microfluidic channel may be exposed to light, while other portions are prevented from being exposed to light, for instance, by the use of masks or filters, or by using a focused beam of light. Accordingly, different portions of the microfluidic channel may exhibit different hydrophobicities, as polymerization does not occur everywhere on the microfluidic channel. As another example, the microfluidic channel may be exposed to UV light by projecting a de-magnified image of an exposure pattern onto the microfluidic channel. In some cases, small resolutions (e.g., 1 micrometer, or less) may be achieved by projection techniques.

Additional details of such coatings and other systems may be seen in Int. Pat. Apl. Ser. No. PCT/US2009/000850, filed Feb. 11, 2009, entitled "Surfaces, Including Microfluidic Channels, With Controlled Wetting Properties," by Weitz, et al., published as WO 2009/120254 on Oct. 1, 2009, and International Patent Application Serial No. PCT/US2009/000850, filed Feb. 11, 2009, entitled "Surfaces, Including Microfluidic Channels, With Controlled Wetting Properties," by Abate, et al., each incorporated herein by reference.

In one embodiment, it may be desirable to slow the release of the active agent by the process of diffusion. In such an embodiment, the release of the ctive agent may be facilitated by mechanical rupture of the microparticles, by thermal breakdown of the shell and hydrogel, or by dissolving the shell and hydrogel of the core of the microparticles.

While microparticles with the first liquid pre-emulsion enable high encapsulation efficiency of the hydrophobic payload, the density mismatch between the payload and the aqueous continuous phase of the first liquid may result in the dispersed payload rising and directly contacting the inner surface of the polymeric shell. This contact may enable the payload to move into the hydrophobic polymer, leading to a rapid leakage and hence limiting the long-term storage of the payload. To achieve long-term storage of the payload, the continuous phase of the first liquid may be modified by the addition of a hydrogel precursor and a photo-initiator to enable the conversion of the continuous phase within the microparticles to a hydrogel, enabling it to act as a physical barrier and preventing direct exposure of the innermost dispersed phase payload with the polymeric shell. As an example a continuous phase of the first liquid may be composed of an aqueous solution of 15% polyethylene glycol diacrylate (PEG-DA, $M_n$=700) with a photo-initiator. In the presence of electromagnetic radiation, the PEG-DA precursor solution can be rapidly polymerized, and/or cross-linked, transforming into an hydrogel.

Certain aspects of the invention are generally directed to techniques for scaling up or "numbering up" devices such as those discussed herein. For example, in some cases, relatively large numbers of devices may be used in parallel, for example at least about 10 devices, at least about 30 devices, at least about 50 devices, at least about 75 devices, at least about 100 devices, at least about 200 devices, at least about 300 devices, at least about 500 devices, at least about 750 devices, or at least about 1,000 devices or more may be operated in parallel. In some cases, an array of such devices may be formed by stacking the devices horizontally and/or vertically. The devices may be commonly controlled, or separately controlled, and can be provided with common or separate sources of various fluids, depending on the application.

Those of ordinary skill in the art will be aware of other techniques useful for scaling up or numbering up devices or articles such as those discussed herein. For example, in some embodiments, a fluid distributor can be used to distribute fluid from one or more inputs to a plurality of outputs, e.g., in one more devices. For instance, a plurality of articles may be connected in three dimensions. In some cases, channel dimensions are chosen that allow pressure variations within parallel devices to be substantially reduced. Other examples of suitable techniques include, but are not limited to, those disclosed in International Patent Application No. PCT/US2010/000753, filed Mar. 12, 2010, entitled "Scale-up of Microfluidic Devices," by Romanowsky, et al., published as WO 2010/104597 on Nov. 16, 2010, incorporated herein by reference in its entirety.

The following documents are incorporated herein by reference in their entirety for all purposes: International Patent Application Serial No.: PCT/US2015/025921, filed: Apr. 15, 2015, Title: Systems and methods for producing droplet emulsions with relatively thin shells; Inventors: David Weitz, Esther Amstad, Laura R. Arriaga; International Patent Publication Number WO 2004/091763, filed Apr. 9, 2004, entitled "Formation and Control of Fluidic Species," by Link et al.; International Patent Publication Number WO 2004/002627, filed Jun. 3, 2003, entitled "Method and Apparatus for Fluid Dispersion," by Stone et al.; International Patent Publication Number WO 2006/096571, filed Mar. 3, 2006, entitled "Method and Apparatus for Forming Multiple Emulsions," by Weitz et al.; International Patent Publication Number WO 2005/021151, filed Aug. 27, 2004, entitled "Electronic Control of Fluidic Species," by Link et al.; International Patent Publication Number WO 2008/121342, filed Mar. 28, 2008, entitled "Emulsions and Techniques for Formation," by Chu et al.; International Patent Publication Number WO 2010/104604, filed Mar. 12, 2010, entitled "Method for the Controlled Creation of Emulsions, Including Multiple Emulsions," by Weitz et al.; International Patent Publication Number WO 2011/028760, filed Sep. 1, 2010, entitled "Multiple Emulsions Created Using Junctions," by Weitz et al.; International Patent Publication Number WO 2011/028764, filed Sep. 1, 2010, entitled "Multiple Emulsions Created Using Jetting and Other Techniques," by Weitz et al.; International Patent Publication Number WO 2009/148598, filed Jun. 4, 2009, entitled "Polymersomes, Phospholipids, and Other Species Associated with Droplets," by Shum, et al.; International Patent Publication Number WO 2011/116154, filed Mar. 16, 2011, entitled "Melt Emulsification," by Shum, et al.; International Patent Publication Number WO 2009/148598, filed Jun. 4, 2009, entitled "Polymersomes, Colloidosomes, Liposomes, and other Species Associated with Fluidic Droplets," by Shum, et al.; International Patent Publication Number WO 2012/162296, filed May 22, 2012, entitled "Control of Emulsions, Including Multiple Emulsions," by Rotem, et al.; International Patent Publication Number WO 2013/006661, filed Jul. 5, 2012, entitled "Multiple Emulsions and Techniques for the Formation of Multiple Emulsions," by Kim, et al.; and International Patent Publication Number WO 2013/032709, filed Aug. 15, 2012, entitled "Systems and Methods for Shell Encapsulation," by Weitz, et al.

Figure 6:
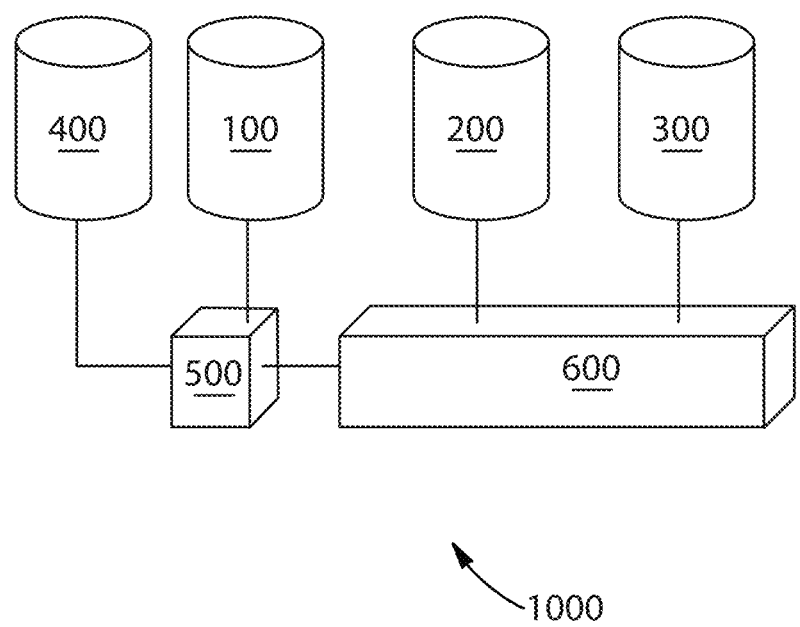
FIG. 6 provides a schematic illustration of an apparatus according to one embodiment of the invention.

In one embodiment, illustrated in FIG. 6, an apparatus 1000 for producing microcapsules may include: a first reservoir 100 containing a first liquid, wherein the first liquid may comprise an emulsion comprising in turn, a dispersed phase and a continuous phase. The first reservoir may be disposed in fluid communication with a plurality of first conduits forming a portion of a plurality of microfluidic devices 600, each of the first conduits having an exit. The apparatus also comprises a second reservoir 200 containing a second liquid, the second reservoir may be disposed in fluid communication with a plurality of second conduits forming a portion of the plurality of microfluidic devices 600. Each of the second conduits at least partly surrounds one of the first conduits. The first and second fluids are substantially immiscible. The apparatus further comprises a third reservoir 300 containing a third liquid, the third reservoir disposed in fluid communication with second conduits. The second and third fluids being substantially immiscible. The apparatus further comprising a plurality of third conduits disposed at least in part within the second conduits downstream of the exits of the first conduits as part of the plurality of microfluidic devices, the third conduits positioned to receive the first liquid exiting the first conduits, the second liquid and the third liquid.

The volume of the reservoirs may range from as little as about 2 ml, to as much as about 6,000 L depending upon the volume of product desired to be produced.

In such an embodiment, the first reservoir may be disposed in switchable fluid communication with the first conduits and the apparatus may further comprise a fourth reservoir 400 containing a fourth liquid, wherein the fourth liquid is an emulsion comprising a dispersed phase and a continuous phase, the fourth reservoir 400 disposed in switchable fluid communication with the first conduits by the activation of valve 500.

In one embodiment, the dispersed phase of the first liquid is substantially miscible with the second liquid and the dispersed phase of the fourth liquid is substantially immiscible with the second liquid.

TEST METHODS

It is understood that the test methods that are disclosed in the Test Methods Section of the present application should be used to determine the respective values of the parameters of Applicants' invention as such invention is described and claimed herein. Furthermore, it is obvious to those skilled in the art that encapsulated benefit agents need to be isolated from the product before using the methods below and isolation will depend not only on the type and form of the product but also on the encapsulated benefit agent shell nature. For example, encapsulated benefit agents comprised in a liquid product might be isolated by centrifugation and redisperse in a non-solvent for the encapsulated benefit agent shell, whilst for encapsulated benefit agents comprised in solid products, a solvent for the binder and non-solvent for the encapsulated benefit agent shell might be use.

(1) Mean Diameter of a Population of Encapsulated Benefit Agents:

A population of encapsulated benefit agents is characterized by a mean diameter ($\overline{D}$) obtained using scanning electron microscopy and computerized image analysis with the ImageJ software program version 1.46r (Rasband, W. S., ImageJ, U. S. National Institutes of Health, Bethesda, Md., USA, http://imagej.nih.gov/ij/, 1997-2012.).

i. A sample of a population of encapsulated benefit agents of about 30 mg is adhered to a bioadhesive stub (e.g., 12.5 mm diameter Aluminium Pin Stub G301, mounted with 12 mm diameter Leit Adhesive Carbon tab, as available from Agar Scientific, Essex, UK), avoiding agglomerations to obtain a single, uniform layer of encapsulated benefit agents on the stub.

ii. A Hitachi TM-1000 Table Top Scanning Electron Microscope (Hitachi High-Technologies Europe GmbH, Germany) is used to take about 10 images per stub using a magnification of about 100×, in order to obtain images of about 500 randomly selected encapsulated benefit agents.

iii. From the 10 images taken, at least 3 images are selected for ImageJ analysis, while ensuring that sufficient images are selected to depict a monolayer of at least 300 encapsulated benefit agents, in total.

iv. Each of the 3 or more images is opened in ImageJ. The images are calibrated and the scale used is in micrometers (μm). Each image is converted to 8-bit grayscale pixel depth, and then automatically thresholded by the software's auto threshold button to create a binary image, whereby pixels representing the encapsulated benefit agents become the foreground objects and regions-of-interest, which are separated from the background pixels. The area (in sq.μm) of each region-of-interest object representing an encapsulated benefit agent, is then measured with ImageJ by selecting "Area" on the "Set Measurement" menu, and within "Area" select "Exclude Edge Particles" and "circularity". Then for "circularity" enter the range of values from about 0.4 to about 1 on the "Analyze Particles" menu.

v. The obtained areas (A, in sq.μm) are recorded and used to calculate the diameter of the encapsulated benefit agents according to following formula:

$d_i = \sqrt{(4A_i/\pi)}$ wherein $d_i$ is the diameter in micrometers and $A_i$ the area obtained from ImageJ for a given encapsulated benefit agent.

vi. Then, diameters ($d_i$) are rank-ordered from largest to smallest size and the mean encapsulated benefit agent size is obtained using following formula:

$$\overline{D} = \frac{\sum_{i=1}^{n} d_i}{n}$$

wherein $\overline{D}$ is the mean encapsulated benefit agent diameter in micrometers, $d_i$ are the individual diameters of the encapsulated benefit agent as calculated above in micrometers and n the total number of encapsulated benefit agent analyzed, using a minimum of 300 encapsulated benefit agents to obtain such mean. Additionally, the $5^{th}$, $50^{th}$ and $95^{th}$ percentile values are also calculated for these diameter datapoints.

(2) Coefficient of Variation of the Diameters of a Population of Encapsulated Benefit Agents:

A population of encapsulated benefit agents is characterized by a diameter coefficient of variation (CoV) corresponding to the ratio between the diameter distribution of said population of encapsulated benefit agents (ie the standard deviation) and the mean encapsulated benefit agent diameter. CoV is obtained as follow:

i. First, the Standard Deviation (STD) of the mean encapsulated benefit agents' diameter is obtained using following formula:

$$STD = \sqrt{\frac{\sum_{i=1}^{n}(d_i - \overline{D})^2}{n}}$$

wherein STD is the standard deviation of diameters in micrometers, $\overline{D}$ is the mean encapsulated benefit agent diameter in micrometers, $d_i$ are the individual diameters of the encapsulated benefit agents in micrometers as calculated above, and n is the total number of encapsulated benefit agents analyzed, using a minimum of 300 encapsulated benefit agents to obtain such STD.

ii. Finally, the coefficient of variation (CoV) of the diameters of a population of encapsulated benefit agents is obtained using following formula:

$$CoV = \frac{STD \cdot 100}{\overline{D}}$$

wherein CoV is the coefficient of variation of the diameters of a population of encapsulated benefit agents in %, STD and $\overline{D}$ are the standard deviation and the mean diameter in micrometers, respectively, as calculated above.

(3) Mean Shell Thickness:

The mean shell thickness is determined by preparing cross-sections of targeted encapsulated benefit agents and measuring the shell thickness under a Scanning Electron Microscope (such as model JSM-6400, available from JEOL Ltd, Tokyo, Japan). Approximately 200 mg of encapsulated benefit agent sample (as dry powder) is mixed with about 1 mL of Optimal Cutting Temperature solution (OCT). In the case of non water-soluble shell materials, the OCT solution can be composed of 10.24% poly vinyl alcohol, 4.26% Poly ethylene glycol and 85.5% non-reactive ingredients. Whereas, for water-soluble shell materials, the OCT solution can be comprised of Poly Propylene Glycol, Poly Ethylene Glycol, Glycerin, Vegetable oil and/or Mineral oil. This OCT solution containing the encapsulated benefit agents suspended in it is immediately frozen by using liquid Nitrogen (−196° C.) and is placed inside a cryostat microtome cooled to −20° C. The cryostat microtome is used to cut sample cross-sections of the frozen suspension, at about 10 μm in thickness. Sections are mounted on room temperature glass microscope slides, where they will instantaneously melt and adhere. After the sections are air-dried at room temperature, they are coated with gold by sputter coating and observed and photographed using a scanning electron microscope (SEM) (such as the JEOL SEM model JSM-6400, available from JEOL Ltd, Tokyo, Japan). From the micrographs obtained of the cross-sections, the shell thickness of 30 encapsulated benefit agents is measured, by selecting 10 encapsulated benefit agents in each of 3 different diameter size fractions. The 3 different diameter size fractions are determined by the $5^{th}$, $50^{th}$ and $95^{th}$ percentile values calculated from the diameter datapoints, as measured under method (1) above. The 3 diameter size fractions are defined (in micrometers) as being: the $5^{th}$ percentile value +/−10% of its value; the $50^{th}$ percentile value +/−10% of its value; and the $95^{th}$ percentile value +/−10% of its value. For each of the 30 encapsulated benefit agents selected, the shell thickness is measured at least at 4 different locations spaced equi-distantly around each shell's circumference, i.e., at 0°, 90°, 180° and 270°, yielding 120 thickness measurements in total. The mean shell thickness ($\bar{S}$) of each capsule is calculated using the at least 4 shell thickness measurements for the respective capsule.

(4)
Microcapsule Stability:

In-situ polymerized microcapsules encapsulating α-pinene are collected, rinsed, and monitored with different time intervals in a closed system with five microcapsules dispersed in 3 mL of DI water after being transferred to a quartz cuvette cell. The cuvette cell is sealed during the leakage study. UV-VIS spectroscopy is used to monitor the leakage profile of various systems in a controlled environment for comparative purposes. Representative systems are selected and the as-prepared and treated microcapsules are transferred to ethanol, to quantitatively determine the amount of α-pinene remaining after each condition tested. The dispersed phase retention fraction is determined according to the stability test after a period of five days. The retention fraction is the % w/w of the α-pinene indicated by the test as remaining in the microcapsules.

The following examples are intended to illustrate certain embodiments of the present invention, but do not exemplify the full scope of the invention.

EXAMPLE 1

This example illustrates encapsulation of an active embedded within secondary compartments to achieve control of the release profile. In this example, a perfume is encapsulated as an illustrative example. Perfume is often a mixture of polar and non-polar components (e.g. fragrant essential oils or aroma compounds). Thus, it can be challenging to encapsulate the perfume in polymer shells which is dispersed in water phase due to their significant solubility in a broad range of solvents, and even in most shell materials (monomer).

Figure 1A:
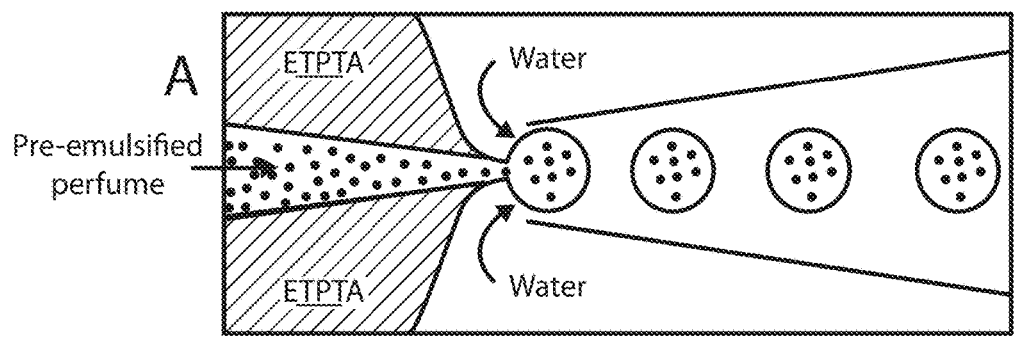
FIGS. 1A-1D illustrate methods useful for forming microparticles, in accordance with one embodiment of the invention.

This example presents a method to encapsulate pre-emulsified perfume in hydrophobic polymer shells, achieving high loading efficiencies, e.g., over 50%. In this particular example, to first form double emulsions (water-in-oil-in-water), three phases were injected into a microcapillary device: 10% PVA (polyvinyl alcohol) in aqueous phase as the continuous phase, ethoxylated trimethylolpropane triacrylate (ETPTA) with a photoinitiator (1%) as the middle phase, and pre-emulsified perfume as an inner phase. See FIG. 1A.

The pre-emulsified perfume was prepared by simple mixing of perfume and surfactant solution. To ensure long-term stability of pre-emulsified perfume, two kinds of surfactants were used, Tween 80 (15.2) and polyvinyl alcohol (PVA), with different hydrophilic lipophilic balances (HLB). For example, in some experiments, pre-emulsified perfume used as an inner phase included 50% perfume, 2.5% PVA, 1% Tween 20 and 46.5% water (all percentages are by weight).

Figure 1B:
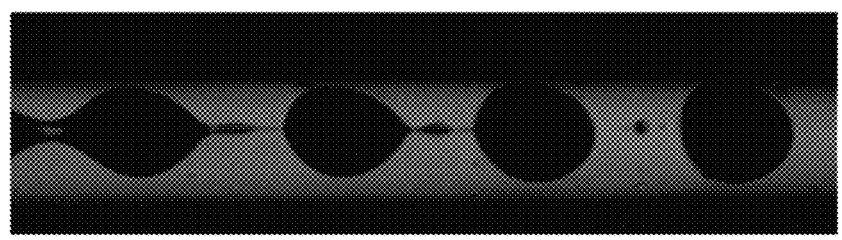
Figures 1C, 1D:
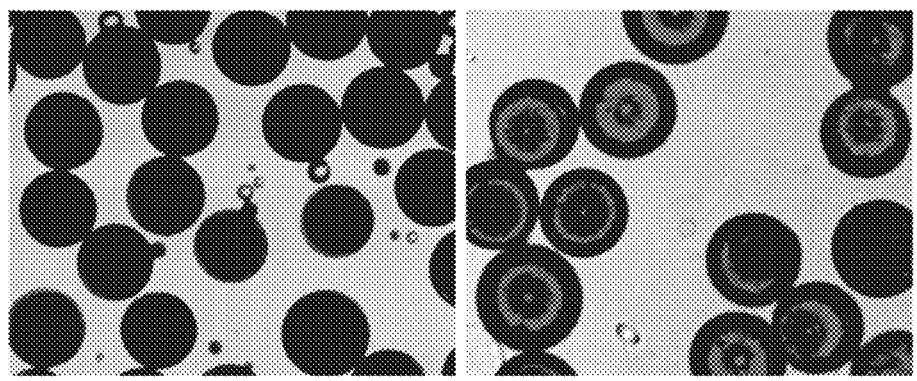

FIG. 1B shows that double emulsions were uniformly formed under jetting conditions, and these droplets were collected in a vial. The double emulsions were exposed to UV light, forming polymer shells containing pre-emulsified perfume (FIGS. 1C and 1D). To demonstrate successful encapsulation of perfume inside, the perfume was stained with Nile Red as a tracer. Overall, high loading efficiencies (e.g., greater than about 50%) of perfume in the polymer shells was achieved by encapsulating pre-emulsified perfume.

EXAMPLE 2

Figure 2:
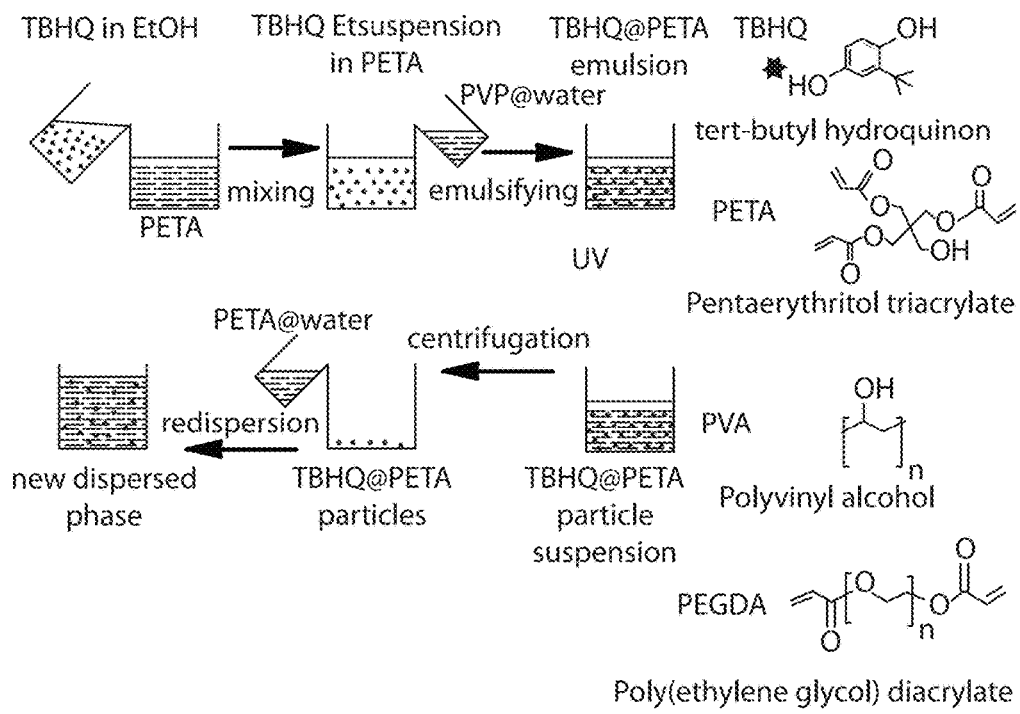
FIG. 2 illustrates the production of a particle suspension, in another embodiment of the invention.

In this example, an antioxidant was encapsulated as another illustrative example. See FIG. 2.

Preparation of THBQ in monomer solution. Antioxidant (tert-butyl hydroquinone, TBHQ, 600 mg) was dissolved in EtOH (1 mL) in a glass vial. To a vial containing a hydrophobic monomer (pentaerythritol triacrylate, PETA, 3 g), and a photoinitiatior (2-hydroxy-2-methylpropiophenone, HMP, 30 mg), the EtOH solution of TBHQ was added. The solution (2 g) was left under vacuum for 6 hours to remove EtOH and a transparent and viscous fluid of monomer with TBHQ dissolved inside was found.

Preparation of water in oil emulsion. To the resulting solution, 8 mL aqueous solution of PVA (10 wt %) was added and the resulting mixture was then placed on vortex for 1 min. After initial mixing, the turbid emulsion was subject to tip sonication under an ice bath for 15 min (40% power, 5 s sonication, 2 s interval).

Synthesis of secondary particle dispersion in water. After sonication, the emulsion was transferred into a syringe (5 mL) and then pumped out at 1 mL/min through a plastic tube to a collection vial. UV light was applied to the outlet of the tube (1 cm above the tube) and as a result, the drops from the emulsion were photo-irradiated and the polymerization of PETA was initiated in the oil phase.

Washing secondary particles. After photo-polymerization, three cycles of centrifuge/re-dispersion was used to remove impurities from the particles dispersion. The pH of the dispersion containing particles (1 mL) was adjusted to 5 using buffer phosphate solution and centrifuged for 2 minutes using 14000 rpm. After the supernatant was carefully removed, 1 mL of buffer solution was added and the resulting dispersion was sonicated for 10 minutes to re-disperse the particles into solvent. This process was repeated 3 times.

Preparation of secondary particles encapsulated droplet. To an aqueous dispersion of secondary particles (1 mL), a polymer solution (9 mL) containing monomer (polyethylene glycol diacrylate, PEGDA Mw 575, 40 wt %), crosslinker (ethoxylated trimethylolpropane triacrylate, ETPTA, MW 912, 5 wt %), and photoinitiator (HMP, 1 wt %) was added. The resulting solution was mixed using vortex for 5 min before subjecting to microfluidic setup as the dispersed phase (see FIG. 1A). A dodecane solution containing 5 wt % of surfactant (EM90, Evonik) was used as the continuous phase.

Figure 5:
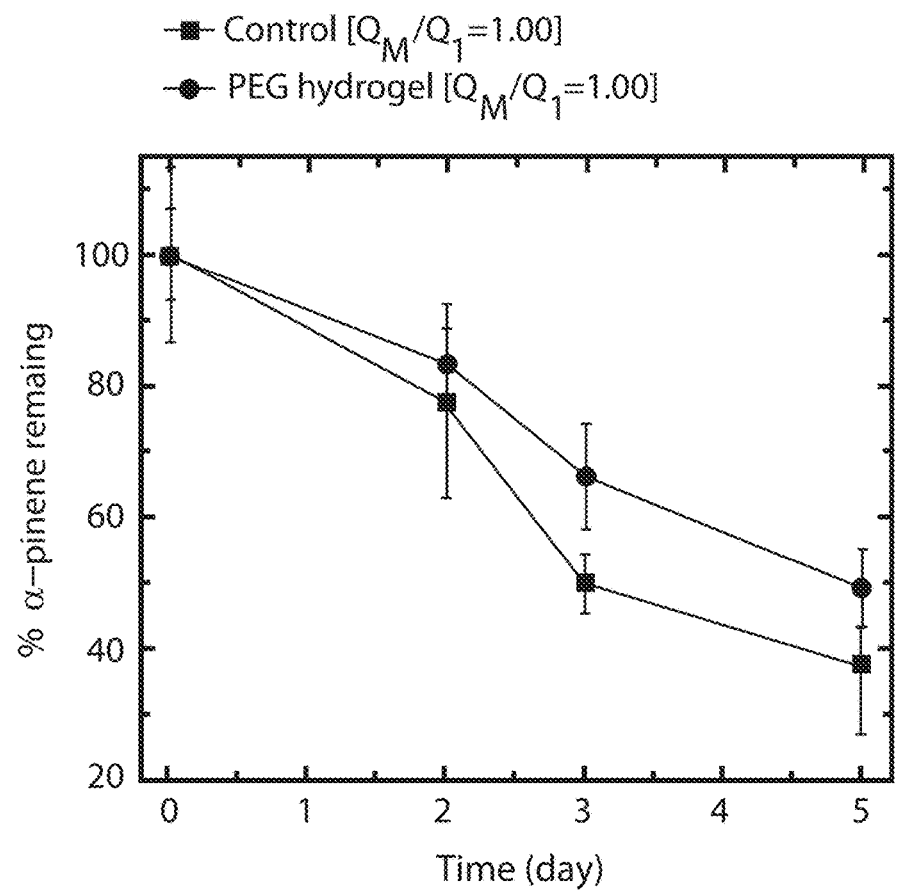
FIG. 5 illustrates data associated with the relative stability of microcapsules having a hydrogel continuous phase and control microcapsules having an aqueous continuous phase.

EXAMPLE 3

α-pinene encapsulated ETPTA microcapsules were prepared with and without a hydrogel network continuous phase in the microcapsules. These microcapsules were rinsed with DI water the continuous aqueous phase carrying the microcapsules was removed. Upon removal of the surrounding water, drastic difference in microcapsule morphology were observed over time. The aqueous phase of fragrance emulsion is replaced by air as the water evaporates for the control microcapsule. No apparent difference is observed for the PEG hydrogel microcapsule. A uniform hydrogel network in PEG hydrogel microcapsule was observed upon breakage. As shown in FIG. 5, the control microcapsules have a dispersed phase retention fraction of less than about 40% w/w after 5 days while the hydrogel continuous phase microcapsules have a dispersed phase retention fraction of about 50% w/w.

The various embodiments set forth above may be used as part of the formulation of a range of consumer products. Such consumer products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners and cleaning implements, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, and tooth whitening.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a plurality of microcapsules, each microcapsule comprising:

a single core comprising a liquid emulsion having a continuous phase and a dispersed phase; and a shell surrounding the single core, wherein the continuous phase comprises a hydrogel;

wherein the dispersed phase comprises a material selected from the group consisting of pr op-2-enyl 3-cyclohexylpropanoate, (4aR,5R,7aS,9R)-octahydro-2,2,5,8,8, 9a-hexamethyl-4h-4a,9-methanoazuleno(5,6-d)-1,3-dioxole, (3aR,5aS,9aS,9bR)-3a,6,6,9a-tetramethyl-2,4,5, 5a,7,8,9,9b-octahydro-1H-benzo[e][1]benzofuran, 4-methoxybenzaldehyde, benzyl 2-hydroxybenzoate, 2-methoxynaphthalene, 3-(4-tert-butylphenyl)propanal, 3a,6,6,9a-tetramethyl-2,4,5,5a,7,8,9,9b-octahydro-1H-benzo[e][1]benzofuran, 3,7-dimethyloct-6-en-1-ol, 3,7-dimethyloct-6-enenitrile, 3-(4-tert-butylphenyl)butanal, 3-(4-propan-2-ylphenyl)butanal, (E)-1-(2,6,6-trimethyl-1-cyclohexa-1,3-dienyl)but-2-en-1-one, decanal, (E)-1-(2,6,6-trimethyl-1-cyclohex-3-enyl)but-2-en-1-one, (5E)-3-methylcyclopentadec-5-en-1-one, 2,6-dimethyloct-7-en-2-ol, ethyl 2-methylpentanoate, ethyl 2-methylbutanoate, 1,3,3-trimethyl-2-oxabicyclo [2,2,2]octane, 2-methoxy-4-prop-2-enylphenol, 3a,4,5, 6,7,7a-hexahydro-4,7-methano-1H-indenyl acetate, 3-(3-propan-2-ylphenyl)butanal, a,4,5,6,7,7a-hexahydro-1H-4,7-methanoinden-1-yl propanoate, (2E)-3, 7-dimethylocta-2,6-dien-1-ol, (12E)-1-oxacyclohexadec-12-en-2-one, [2-[1-(3,3-dimethylcyclohexyl) ethoxy]-2-methylpropyl]propanoate, hexyl acetate, 2-(phenylmethylidene)octanal, hexyl 2-hydroxybenzoate, (E)-4-(2,6,6-trimethyl-1-cyclohex-2-enyl)but-3-en-2-one, (E)-4-(2,6,6-trimethyl-1-cyclohexenyl)but-3-en-2-one, (E)-3-methyl-4-(2,6,6-trimethyl-1-cyclohex-2-enyl)but-3-en-2-one, 1-(2,3,8,8-tetramethyl-1,3,4,5,6,7-hexahydronaphthalen-2-yl) ethanone, propan-2-yl 2-methylbutanoate, (1R,2S,5R)-5-methyl-2-propan-2-ylcyclohexan-1-ol, (E)-2-ethyl-4-(2,2,3-trimethyl-1-cyclopent-3-enyl)but-2-en-1-ol, 2,4-dimethylcyclohex-3-ene-1-carbaldehyde, 3,7-dimethylocta-1,6-dien-3-ol, 3,7-dimethylocta-1,6-dien-3-yl acetate, 1-((3R,3aS,7R,8aS)-2,3,4,7,8,8a-hexahydro-3,6,8,8-tetramethyl-1H-3a,7-methanoazulen-5-yl)-ethanone, methyl 3-oxo-2-pentylcyclopentaneacetate, 2-methylundecanal, 2-[2-(4-methyl-1-cyclohex-3-enyl)propyl]cyclopentan-1-one, 1-(5,5-dimethyl-1-cyclohexenyl)pent-4-en-1-one, 2-cyclohexylidene-2-phenylacetonitrile, 2-phenylethanol, 3,7-dimethyloctan-3-ol, 5-heptyloxolan-2-one, (2-tert-butylcyclohexyl)acetate, (E)-4-methyldec-3-en-5-ol, (4-tert-butylcyclohexyl)acetate, decahydro-2,2,6, 6,7,8,8-heptamethyl-2H-indeno(4,5-b)furan, 17-oxacycloheptadec-6-en-1-one, pentyl 2-hydroxybenzoate, benzyl acetate, 4-phenylbutan-2-one, 2-methoxynaphthalene, 1,7,7-trimethylbicyclo[2.2.1]heptan-2-one, 1,1,2,3,3-pentamethyl-2,5,6,7-tetrahydro-inden-4-one, 1H-3a,7-Methanoazulene, octahydro-6-methoxy-3,6,8, 8-tetramethyl, [(Z)-hex-3-enyl]acetate, [(Z)-hex-3-enyl]2-hydroxybenzoate, (9Z)-cycloheptadec-9-en-1-one, chromen-2-one, cyclohexyl 2-hydroxybenzoate, ethyl 3-methyl-3-phenyloxirane-2-carboxylate, 3-ethoxy-4-hydroxybenzaldehyde, 1,4-dioxacycloheptadecane-5,17-dione, 16-oxacyclohexadecan-1-one, diethyl cyclohexane-1,4-dicarboxylate, 1-(5,5-dimethyl-1-cyclohexenyl)pent-4-en-1-one, [(2E)-3,7-dimethylocta-2,6-dienyl]acetate, 3-(1,3-benzodioxol-5-yl)-2-methylpropanal, 1,3-benzodioxole-5-carbaldehyde, 6-(pent-3-en-1-yl)tetrahydro-2H-pyran-2-one, [(1R, 2S)-1-methyl-2-[[(1R,3 S,5 S)-1,2,2-trimethyl-3-bicyclo[3.1.0]hexanyl]methyl]cyclopropyl]methanol, (Z)-3,4,5,6,6-pentamethyl-hept-3-en-2-one, dodecanal, 3,7-dimethylnona-2,6-dienenitrile, (2S)-2-aminopentanedioic acid, methyl 2,4-dihydroxy-3,6-dimethylbenzoate, 2,6-dimethyloct-7-en-2-ol, 4-(4-hydroxy-4-methylpentyl)cyclohex-3-ene-1-carbaldehyde, 1-naphthalen-2-ylethanone, 4-methyl-2-(2-methylprop-1-enyl)oxane, 1H-Indene-ar-propanal, 2,3-dihydro-1,1-dimethyl-(9CI), nonanal, octanal, 2-phenylethyl 2-phenylacetate, 3-methyl-5-phenylpentan-1-ol, 4-methyl-2-(2-methylpropyl)oxan-4-ol, 1-oxacycloheptadecan-2-one, 1-(spiro[4.5]dec-7-en-7-yl)pent-4-en-1-one, 2-(4-methyl-1-cyclohex-3-enyl)propan-2-ol, 1-methyl-4-propan-2-ylidenecyclohexene, (4-methyl-1-propan-2-yl-1-cyclohex-2-enyl)acetate, 1,2-dimethylcyclohex-3-ene-1-carbaldehyde, undec-10-enal, [(4Z)-1-cyclooct-4-enyl]methyl carbonate, 8-methyl-1,5-benzodioxepin-3-one, nona-2,6-dienal, (5Z)-cyclohexadec-5-en-1-one, 2,6,10-trimethylundec-9-enal, prop-2-enyl hexanoate, (E)-1-(2,6,6-trimethyl-1-cyclohex-2-enyl)but-2-en-1-one, 3-phenylprop-2-en-1-ol, 3,7-dimethylocta-2,6-dienal, 3,7-dimethyloct-6-enyl acetate, [2-(2-methylbutan-2-yl)cyclohexyl]acetate, 3a,4,5,6,7,7a-hexahydro-4,7-methano-1H-inden-5-yl 2-methyl propanoate, 2-pentylcyclopentan-1-ol, (E)-dec-4-enal, 2-pentylcyclopentan-1-one, 2-methoxy-4-propylphenol, methyl 2-hexyl-3-oxocyclopentane-1-carboxylate, phenoxybenzene, ethyl 3-phenylprop-2-enoate, (E)-2-ethyl-4-(2,2,3-trimethyl-1-cyclopent-3-enyl)but-2-en-1-ol, 3-(4-ethylphenyl)-2,2-dimethylpropanal, 4-methyl-2-(2-methylpropyl)oxan-4-ol, 2-methyldecanenitrile, 5-hexyloxolan-2-one, 5-(diethoxymethyl)-1,3-benzodioxole, 7-hydroxy-3,7-dimethyloctanal, (E)-4-(2,5,6,6-tetramethyl-1-cyclohex-2-enyl)but-3-en-2-one, [(1R,4S,6R)-1,7,7-trimethyl-6-bicyclo[2.2.1]heptanyl]acetate, 6-butan-2-ylquinoline, 2-methoxy-4-prop-1-en-2-ylphenol, (NE)-N-[(6E)-2,4,4,7-tetramethylnona-6,8-dien-3-ylidene]hydroxylamine, (4-propan-2-ylcyclohexyl)-methanol, 2,6-dimethylhept-5-enal, (1R,2S,5R)-5-methyl-2-propan-2-ylcyclohexan-1-ol, ethyl 2-(2-methyl-1,3-dioxolan-2-yl)acetate, 1-phenylethyl acetate, 1-(3,5,5,6,8,8-hexamethyl-6,7-dihydronaphthalen-2-yl)ethanone, 6-butyloxan-2-one, 2,4-dimethyl-2-(5,6,7,8-tetrahydro-5,5,8,8-tetramethyl-2-naphthalenyl)-1,3-dioxolane, (2R,4S)-2-methyl-4-propyl-1,3-oxathiane, 4-(4-hydroxyphenyl)butan-2-one, 3-methyl-5-phenylpentan-1-ol, 4-((1R,5S)-6,6-dimethylbicyclo[3.1.1]hept-2-en-2-yl)-3,3-dimethylbutan-2-one, 3-methylbut-2-enyl acetate, dec-9-en-1-ol, 5-(3-methylphenyl)pentan-1-ol, 3,7-dimethyloctan-3-ol, 1-methoxy-4-[(E)-prop-1-enyl]benzene, 4-hydroxy-3-methoxybenzaldehyde, 9-acetyl-2,6,6,8-tetramethyltricyclo(5.0.3.1.01,5)undec-8-ene, 2,5-dioxacyclohexadecane-1,6-dione, and mixtures thereof, and the continuous phase comprises a material selected from the group consisting of: water, glycerine, formamide, dimethyl formamide, dimethyl sulfoxide, polyethylene glycol, propylene glycol, fluorinated oils, and mixtures thereof.

\* \* \* \* \*